United States Patent
Platzek et al.

(10) Patent No.: US 12,398,144 B2
(45) Date of Patent: Aug. 26, 2025

(54) PHOTOCHEMICAL PROCESS FOR PRODUCING (4R,4S)-4-(4-CYANO-2-METHOXYPHENYL)-5-ETHOXY-2,8-DIMETHYL-1,4-DIHYDRO-1,6-NAPHTHYRIDIN-3-CARBOXAMIDE

(71) Applicant: Bayer Aktiengesellschaft, Leverkusen (DE)

(72) Inventors: Johannes Platzek, Berlin (DE); Kai Lovis, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 328 days.

(21) Appl. No.: 17/769,402

(22) PCT Filed: Oct. 12, 2020

(86) PCT No.: PCT/EP2020/078614
§ 371 (c)(1),
(2) Date: Apr. 15, 2022

(87) PCT Pub. No.: WO2021/074079
PCT Pub. Date: Apr. 22, 2021

(65) Prior Publication Data
US 2024/0150357 A1 May 9, 2024

(30) Foreign Application Priority Data
Oct. 17, 2019 (EP) .................................. 19203824

(51) Int. Cl.
*C07D 487/04* (2006.01)
(52) U.S. Cl.
CPC ................. *C07D 487/04* (2013.01)
(58) Field of Classification Search
CPC .... C07D 487/04; C07D 471/04; C07B 55/00; C07B 2200/07; A61K 31/4375
See application file for complete search history.

(56) References Cited

U.S. PATENT DOCUMENTS

| | | | |
|---|---|---|---|
| 8,436,180 B2 | 5/2013 | Barfacker et al. | |
| 10,059,707 B2 | 8/2018 | Platzek et al. | |
| 10,392,384 B2 | 8/2019 | Platzek et al. | |
| 12,054,481 B2 | 8/2024 | Platzek et al. | |
| 2016/0289216 A1 | 10/2016 | Jones et al. | |
| 2018/0237414 A1 | 8/2018 | Platzek et al. | |

FOREIGN PATENT DOCUMENTS

| | | |
|---|---|---|
| CN | 108473488 A | 8/2018 |
| WO | 2008104306 A2 | 9/2008 |
| WO | 2016016287 A2 | 2/2016 |
| WO | 2017032627 A1 | 3/2017 |
| WO | 2017032678 A1 | 3/2017 |
| WO | 2019206909 A1 | 10/2019 |

OTHER PUBLICATIONS

Ahmad, W. et al., "Photoinduced Aromatization of Asymmetrically Substituted 1,4-Dihydropyridine Derivative Drug Cilnidipine," International Journal of Photochemistry, 2014, Article ID 176989, 4 pages.
Al-Jalal, N.A. et al., "Photochemistry of 1,4-Dihydropyridine Derivatives: Diradical Formation, Delocalization and Trapping as a Route to Novel Tricyclic and Tetracyclic Nitrogen Heterocyclic Ring Systems," Molecules 2016, 21, 866, 9 pages.
Bärfacker, L. et al., "Discovery of BAY 94-8862: A Nonsteroidal Antagonist of the Mineralocorticoid Receptor for the Treatment of Cardiorenal Diseases," ChemMedChem 2012, 7, pp. 1385-1403.
Biellmann, J.F. et al., "Photolysis of 2,6-Dimethyl-3,5-Dicarboethoxy-1,4-Dihydropyridine-4-Carboxylic Acid," Tetrahedron 1972, 28, pp. 5911-5921.
Fasani, E. et al., "Intramolecular Electron Transfer in the Photochemistry of Some Nitrophenyldihydropyridines," J. Org. Chem. 2006, 71, pp. 2037-2045.
Freytag, H. et al., "Einwirkung ultravioletter Strahlen auf Pyridin: Ein neuer Nachweis einiger primärer aromatischer Amine und des Pyridins," J. Prakt. Chem. 1932, 135, pp. 15-35.
Freytag, H. et al., "Einwirkung ultravioletter Strahlen auf Pyridin: Über Photopyridinbildung im Spektrum," J. Prakt. Chem. 1933, 136, pp. 288-292.
Freytag, H., "Einwirkung ultravioletter Strahlen auf Pyridin: Über den qualitativen Nachweis weiterer primärer aromatischer Amine, über das Verhalten von Pyridinderivaten im UV-Licht und über die Natur des "Photopyridins"," J. Prakt. Chem. 1933, 139, pp. 44-62.
International Search Report of PCT/EP2020/078614 (filed on Oct. 12, 2020 by Bayer Aktiengesellschaft). International Search completed on Nov. 9, 2020 and mailed on Nov. 23, 2020; 18 pages.
Jin, M.-Z. et al., "Novel photoinduced aromatization of Hantzsch 1,4-dihydropyridines," Chem. Commun. 1998, pp. 2451-2452.
Joussot-Dubien, J. et al., "Reversible Photolysis of Pyridine in Aqueous Solution," Tetrahedron Letters, 1967, No. 44, pp. 4389-4391.
Kira, A. et al., "Studies of the Photoreduction of Acridine in Ethanol by the Flash Technique," Bulletin of the Chemical Society of Japan 1966, 13, pp. 1221-1227.

(Continued)

*Primary Examiner* — Joseph K Mckane
*Assistant Examiner* — Ashli Ariana Chicks
(74) *Attorney, Agent, or Firm* — Quarles & Brady LLP

(57) ABSTRACT

The invention relates to a method for preparing racemic (4R,4S)-4-(4-cyano-2-methoxyphenyl)-5-ethoxy-2,8-dimethyl-1,4-dihydro-1,6-naphthyridine-3-carboxamide of the formula (I) from the enantiomers (Ia) or (Ib); a method for preparing (4S)-4-(4-cyano-2-methoxyphenyl)-5-ethoxy-2,8-dimethyl-1,4-dihydro-1,6-naphthyridine-3-carboxamide of the formula (Ia); a method for preparing racemic (4R,4S)-4-(4-cyano-2-methoxyphenyl)-5-ethoxy-2,8-dimethyl-1,4-dihydro-1,6-naphthyridine-3-carboxamide of the formula (I) from the pyridine of the formula (II). The objects of the invention have in common the irradiation of the compound of the formulae (Ia), (Ib) and/or (II) with light in a suitable solvent, or solvent mixture, in the presence of a base. The compounds of the formulae (Ia), (Ib) and/or (II) are intermediates, by-products or target compounds in the synthesis of finerenone (compound according to formula (Ia)).

15 Claims, No Drawings

(56) References Cited

OTHER PUBLICATIONS

Kira, A. et al., "Photochemical Reaction between Acridine and Acridan in the Presence and in the Absence of Oxygen. II. Studies by the Flash Technique," Bulletin of the Chemical Society of Japan 1967, 40(11), pp. 2486-2492.

Koizumi, M. et al., "Primary Processes in the Photoreduction of Acridine in Various Alcohols," Bulletin of the Chemical Society of Japan, 1968, 41(5), pp. 1056-1063.

Leuschner, R. et al., "The 1-Hydro-2,6-Dimethyl-3,5-Dicyanopyridinyl Radical in Solution: Mechanisms of Photochemical Formation and Kinetics of Disappearance by Self-Combination," Journal of Photochemistry 1986, 33, pp. 321-331.

Maafi, M. et al., "Quantification of Unimolecular Photoreaction Kinetics: Determination of Quantum Yields and Development of Actinometers—The Photodegradation Case of Cardiovascular Drug Nisoldipine," International Journal of Photoenergy 2015, 12 pages.

Memarian, H.R. et al., "Synthesis and Photochemistry of Novel 3,5-Diacetyl-1,4-dihydropyridines," Monatshefte für Chemie 2002, 133, pp. 661-667.

Pávez, P. et al., "Photophysics and Photochemical Studies of 1,4-Dihydropyridine Derivatives," Photochemistry and Photobiology, 2007, 83, pp. 722-729.

Shibuya, J. et al., "Photochemical Reaction of 2,4,4,6-Tetrasubstituted 1,4-Dihydropyridines in Deaerated Media: Photocolouration and Photorearrangement accompanying Dehydrogenation," J. Chem. Soc. Perkin Trans. II 1988, pp. 1607-1612.

Subramani, H.J. et al., "Optimization of reactive SMB and Varicol systems," Computers and Chemical Engineering, 2003, 27, pp. 1883-1901.

Van Bergen, T.J. et al., "Photochemistry of 3,5-Dicarboalkoxypyridines. Reduction and Rearrangement," Journal of the American Chemical Society 1972, 94(24), pp. 8451-8471.

Whitten, D.G. et al., "Photochemistry of Aza Aromatics. Identification of the Reactive Intermediate in the Photoreduction of Acridine," Journal of American Chemical Society 1971, 93(4), pp. 961-966.

PHOTOCHEMICAL PROCESS FOR PRODUCING (4R,4S)-4-(4-CYANO-2-METHOXYPHENYL)-5-ETHOXY-2,8-DIMETHYL-1,4-DIHYDRO-1,6-NAPHTHYRIDIN-3-CARBOXAMIDE

The invention relates to a method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

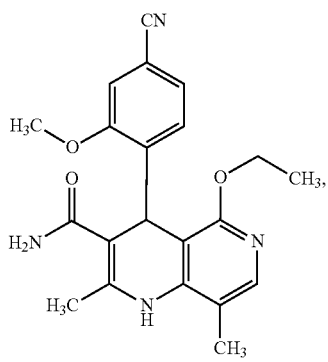

(I)

from the enantiomers Ia or Ib, comprising the step (i) of
(i) irradiating the enantiomers of the formula (Ia) and/or (Ib)

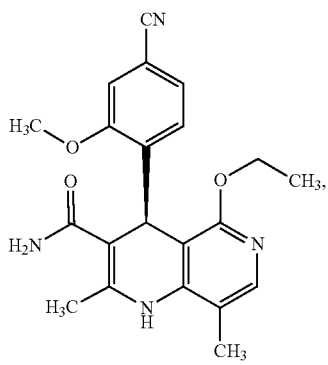

(Ia)

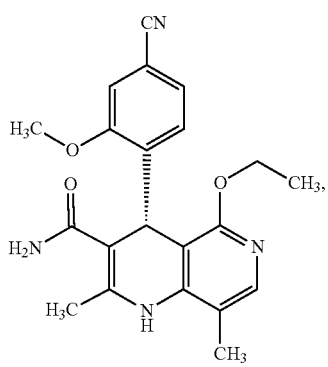

(Ib)

in a suitable solvent or solvent mixture, and also in the presence of a base.

The invention further relates to a method for preparing (4S)-4-(4-cyano-2-methoxyphenyl)-5-ethoxy-2,8-dimethyl-1,4-dihydro-1,6-naphthyridine-3-carboxamide of the formula (Ia), comprising the steps (ii), (iii) and (iv):

(ii) irradiating the compound of the formula (Ib)

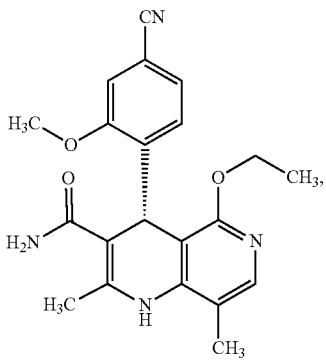

(Ib)

with light in a suitable solvent or solvent mixture in the presence of a base, wherein the compound of the formula (Ib) is converted to a racemic compound of the formula (I)

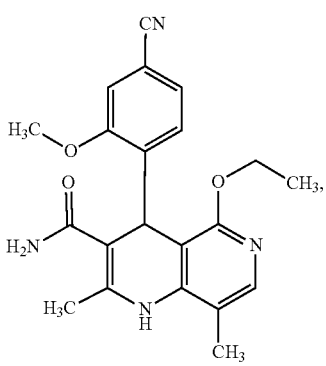

(I)

(iii) optical resolution of this racemic compound (I) from step (ii) using a chiral tartaric acid ester of the formula (III)

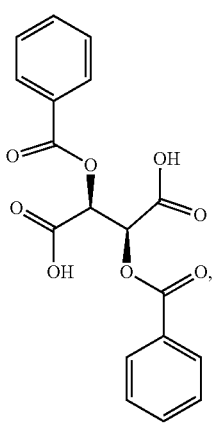

(III)

in a spirits/water mixture, wherein the diastereomeric salt (IVa)

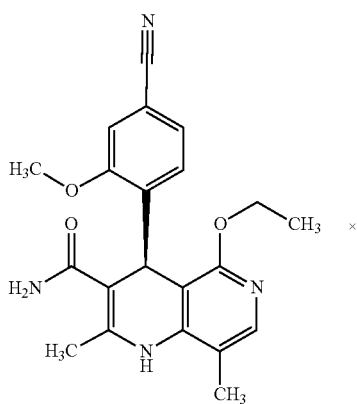

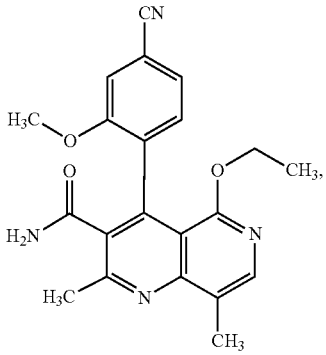

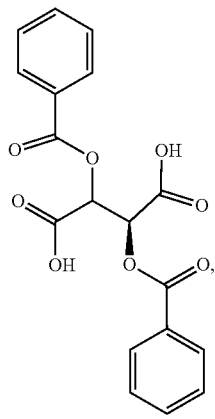

is formed, and (iv) treating the diastereomeric salt (IVa) from step (iii) with a base, wherein the compound of the formula (Ia) is formed.

The invention also relates to a method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

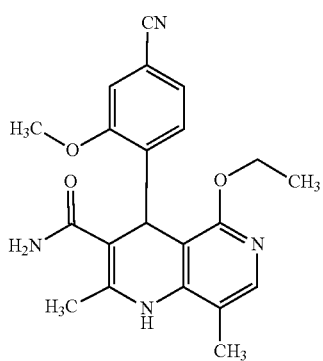

from the pyridine of the formula (II)

comprising the step (vi):

(vi) irradiating the compound of the formula (II) with light in a suitable solvent, or solvent mixture, in the presence of a base, wherein the compound according to formula (I) is formed.

The objects of the invention therefore have in common the irradiation of the compound of the formulae (Ia), (Ib) and/or (II) with light in a suitable solvent, or solvent mixture, in the presence of a base (cf. steps (i), (ii) or (vi)). The compounds of the formulae (Ia), (Ib) and/or (II) are intermediates, by-products or target compounds in the synthesis of finerenone (compound according to formula (Ia)). Here, where reference is made to the compound according to formula (I), then this means racemic (4R,4S)-4-(4-cyano-2-methoxyphenyl)-5-ethoxy-2,8-dimethyl-1,4-dihydro-1,6-naphthyridine-3-carboxamide or the racemic compound according to formula (I) depicted below:

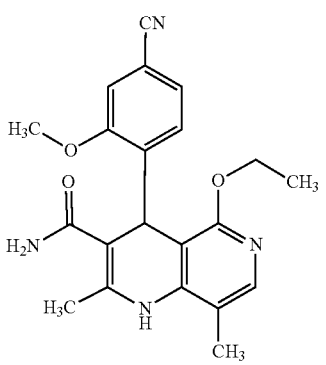

Here, where reference is made to "finerenone", the "compound according to formula (Ia)", "antipode (Ia)", or the "enantiomer (Ia)", then this means (4S)-4-(4-cyano-2-methoxyphenyl)-5-ethoxy-2,8-dimethyl-1,4-dihydro-1,6-naphthyridine-3-carboxamide or the compound according to formula (Ia)

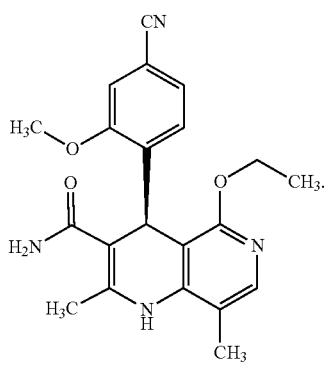

(Ia)

Where reference is made to "enantiomeric compound (Ib)", enantiomer (Ib)", antipode (Ib), "wrong enantiomer" or "wrong enantiomer (Ib)", then this means rac-(4R)-4-(4-cyano-2-methoxyphenyl)-5-ethoxy-2,8-dimethyl-1,4-dihydro-1,6-naphthyridine-3-carboxamide or the compound according to formula (Ib) depicted below

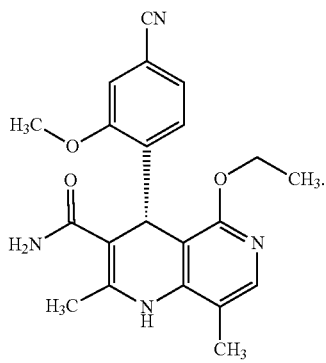

(Ib)

Where reference is made to "antipodes of compound according to formula (I)", then this means the compounds of the formulae (Ia) and (Ib) as defined above.

Where reference is made to "spirits", this means denatured ethanol.

The abbreviation "h" stands for "hour",

Finerenone (Ia) acts as a nonsteroidal antagonist of the mineralocorticoid receptor and can be used as an agent for prophylaxis and/or treatment of cardiovascular and renal disorders such as heart failure and diabetic nephropathy.

The compound of the formula (Ia) and the preparation process therefor are described in WO 2008/104306 A1 and ChemMedChem 2012, 7, 1385, and also in WO 2016/016287 A1. In order to arrive at the compound of the formula (Ia) and (Ib), the racemic mixture of the amides (I) has to be separated into the antipodes of the formula (Ia) and (Ib), since only the antipode of the formula (Ia) is pharmacologically active.

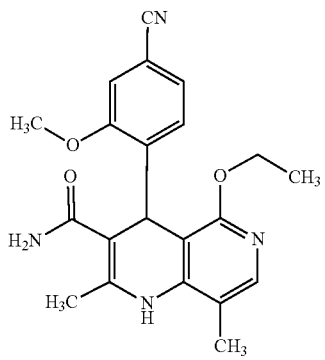

(I)

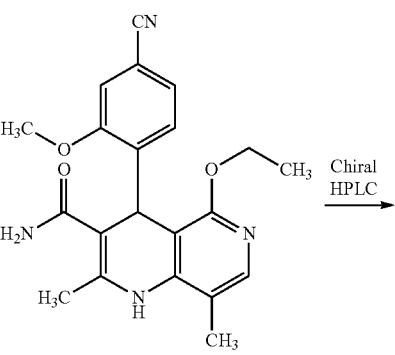

racemic
(I)

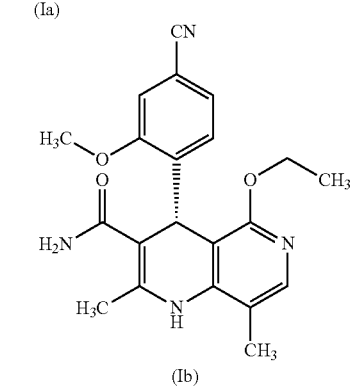

(Ia)

+

(Ib)

In the published research scale synthesis, a specifically synthesized chiral phase was used for this purpose (prepared in-house), which comprised N-(dicyclopropylmethyl)-$N^2$-methacryloyl-D-leucinamide as chiral selector. It has been found that the separation can also be performed on a readily commercially available phase. This is the Chiralpak AS-V phase, 20 m. The eluent used was a mixture of methanol/acetonitrile 60:40. In this case, the chromatography may be carried out on a conventional chromatography column, but preferably the techniques known to those skilled in the art such as SMB or Varicol (Computers and Chemical Engineering 27 (2003) 1883-1901) are used.

The compound of the formula (Ia) and the process for the preparation thereof are described in WO 2008/104306 A1 and ChemMedChem 2012, 7, 1385 and also in WO 2016/016287 A1, both publications disclosing a detailed discussion of the research synthesis.

In the publication ChemMedChem 2012, 7, 1385, which discloses the research scale synthesis of the compound of the formula (Ia), the compound of the formula (Ia) is prepared in 10 stages starting from vanillin with an overall yield of 3.76% of theory.

In order to arrive at the compound of the formula (Ia), the racemic mixture of the amides rac-(I) have to be separated into the antipodes of the formula (La) and (Ib). In the published research scale synthesis, a specifically synthesized chiral phase was used for this purpose (prepared in-house), which comprised N-(dicyclopropylmethyl)-$N^2$-methacryloyl-D-leucinamide as chiral selector. This selector was prepared in a multi-stage process and then polymerized on special silica gel. Methanol/ethyl acetate served as eluent. A major disadvantage of this method was the very low loading, 30 mg per separation on a 500*63 mm chromatography column, such that there was a high need to find as effective a separation method as possible which allows separation of antipodes to be performed in the multi-tonne range. It has been described in WO 2008/104306 A1 that the separation can also be performed on a readily commercially available phase. This is the Chiralpak AS-V phase, 20 μm. The eluent used was a mixture of methanol/acetonitrile 60:40. This mixture has the major advantage that it can be recovered as eluent after distillative work-up having the identical composition (60:40 corresponds to the azeotrope). A very efficient process is achieved in this way in which the yield of the separation is >47% of theory (50% is theoretically possible). The optical purity here is >93% e.e. but preferably >98.5% e.e. In this case, the chromatography may be carried out on a conventional chromatography column, but preferably the techniques known to those skilled in the art such as SMB or Varicol (Computers and Chemical Engineering 27 (2003) 1883-1901) are used. For instance, ca. 500 kg of the racemic amide rac-(I) was separated using an SMB system, in which a yield of 48% was achieved. The product is obtained as a 3-8%, preferably 5-7% solution in a mixture of methanol/acetonitrile 30:70 and can be used directly in "final processing".

Here, for example, where reference is made to a 3% solution, then this therefore means that 3 g of the compound is dissolved in 100 mL of the solvent.

In the figures for the solvent ratios, the ratio means volume to volume (v/v). A solvent mixture consisting of, for example, methanol/acetonitrile 30:70, comprises 30 ml of methanol and 70 ml of acetonitrile. The volume is thus based on the total volume of the solvent.

Other solvent mixture ratios of acetonitrile to methanol are also conceivable (90:10 to 10:90). Alternatively, other solvent mixtures can also be used, however, such as acetonitrile/ethanol in mixture ratios from 10:90 to 90:10, for the SMB separation. The particular solvent ratio depends partly on the technical properties of the SMB system and must be adjusted, if appropriate (e.g. varying flow rate, recycling of the solvent on a thin film evaporator).

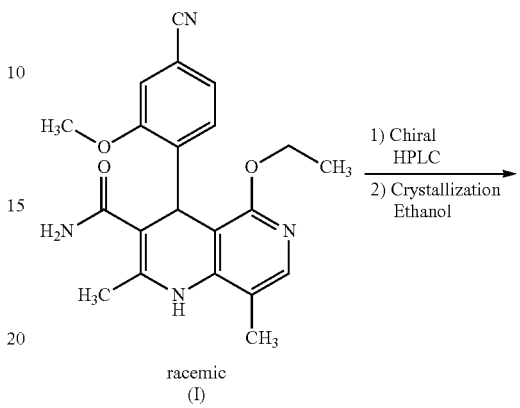

racemic
(I)

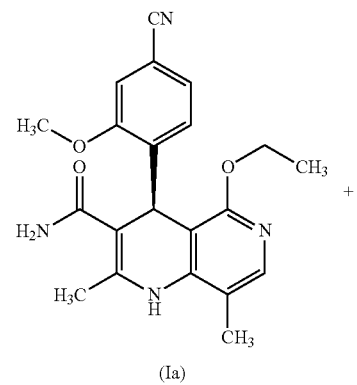

(Ia)

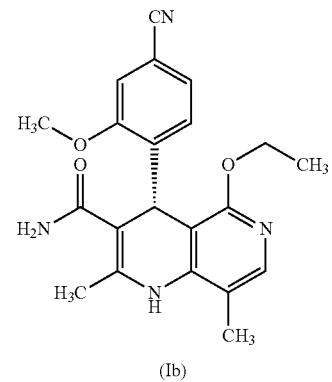

(Ib)

As well as the target compound finerenone (Ia), the enantiomeric compound (Ib) is also obtained in virtually the same yield.

In summary, the invention relates to:

(1) A method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

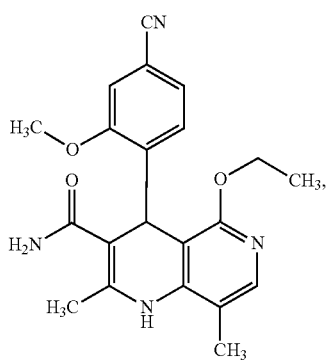

(I)

from the enantiomers Ia or Ib, comprising the step (i) of
(i) irradiating the enantiomers of the formula (Ia) and/or (Ib) in a suitable solvent or solvent mixture, and in the presence of a base;

(2) A method for preparing (4S)-4-(4-cyano-2-methoxyphenyl)-5-ethoxy-2,8-dimethyl-1,4-dihydro-1,6-naphthyridine-3-carboxamide of the formula (Ia), comprising the steps (ii), (iii) and (iv):
  (ii) irradiating the compound of the formula (Ib) with light in a suitable solvent or solvent mixture in the presence of a base, wherein the compound of the formula (Ib) is converted to a racemic compound of the formula (I),
  (iii) optical resolution of this racemic compound (I) from step (ii) using a chiral tartaric acid ester of the formula (III) in a spirits/water mixture, wherein the diastereomeric salt (IVa) is formed, and
  (iv) treating the diastereomeric salt (IVa) from step (iii) with a base, wherein the compound of the formula (Ia) is formed;

(3) A method for preparing racemic (4R,4S)-4-(4-cyano-2-methoxyphenyl)-5-ethoxy-2,8-dimethyl-1,4-dihydro-1,6-naphthyridine-3-carboxamide of the formula (I) from the pyridine of the formula (II) comprising the step (vi):
  (vi) irradiating the compound of the formula (II) with light in a suitable solvent, or solvent mixture, in the presence of a base, wherein the compound according to formula (I) is formed.

The objects of the invention therefore have in common the irradiation of the compound of the formulae (Ia), (Ib) and/or (II) with light in a suitable solvent, or solvent mixture, in the presence of a base (cf. steps (i), (ii) or (vi)). The compounds of the formulae (Ia), (Ib) and/or (II) are intermediates, by-products or target compounds in the synthesis of finerenone (compound according to formula (Ia)).

In summary, the method according to the invention offers, inter alia, the following advantages and technical effects:
  the wrong enantiomer (Ib) may be converted in a simple manner to the target compound finerenone (Ia); this is cost-effective since the wrong enantiomer (Ib) does not have to be destroyed, but rather enables this undesired by-product to be used in finerenone synthesis by converting the compound of the formula (Ib) to a racemic mixture of the formula (I), in order to subject said racemic mixture again to an enantiomer separation by means of SMB or to an optical resolution, for example using (+)-dibenzoyltartaric acid as described above.
  It is no longer necessary to carry out several complex stages, as are described in the prior art: instead of 3 process steps (as in the case of electrochemistry described in, for example, WO 2017032678 A1), a simplified procedure is reached which, under mild conditions (light), leads directly to racemization of the wrong enantiomer (Ib) and therefore results in the racemate (I).
  the reaction (cf. steps (i), (ii) or (vi)), depending on the batch size, may be conducted in batch mode or else as a flow process: the reaction may therefore be adjusted without difficulty to the appropriate industrial conditions in a simple manner.
  starting from the wrong enantiomer (Ib), yields of 50%-75% of theory of the racemate (I) are achieved and chemical purities are very high, it being possible to obtain purities of up to 99.1% (HPLC, area). The enantiomeric excess is <1-2%. A racemate (I) thus obtained may be successfully used in a subsequent racemate resolution method, be it an SMB or optical resolution using dibenzoyltartaric acid, and corresponds to the demands of the required specifications with respect to purity and enantiomeric excess.

Starting from the pyridine derivative (II), yields of 60%-90% of theory of the racemate (I) are achieved. The chemical purities are very high, it being possible to obtain purities of up to >95% (HPLC, area). The enantiomeric excess is <1-2%. A material thus obtained may be successfully used in a subsequent racemate resolution method, be it an SMB or optical resolution using dibenzoyltartaric acid, and corresponds to the demands of the required specifications with respect to purity and enantiomeric excess.

The novel method according to the invention is characterized by high efficiency with respect to yield and chemical purity. The method is environmentally friendly since light is used as the actual "reagent". The method is scalable up to an industrial scale, since photoreactors in the flow process have been used in industry for a long time, that is to say no special equipment is needed in contrast to the electrochemistry described above. Therefore, this novel inventive method exhibits enormous economic advantages compared to the prior art.

The present invention relates to a novel process for preparing racemic (4R,4S)-4-(4-cyano-2-methoxyphenyl)-5-ethoxy-2,8-dimethyl-1,4-dihydro-1,6-naphthyridine-3-carboxamide of the formula (I)

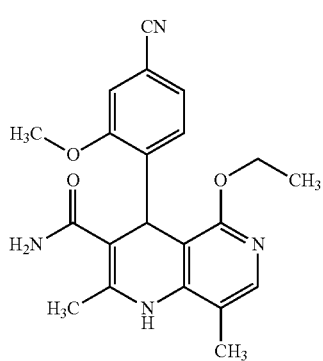

(I)

from the enantiomers Ia or Ib

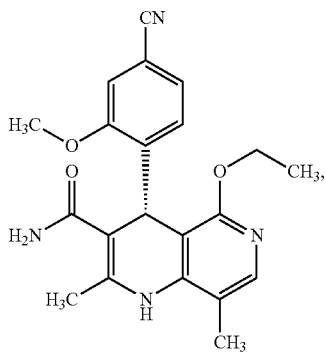
(Ib)

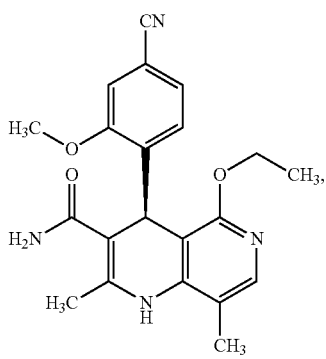
(Ia)

by irradiation with light at a temperature of 0° C. to 100° C. in a suitable solvent, or solvent mixture, and in the presence of a base.

Preference is given in the context of the present invention to a method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

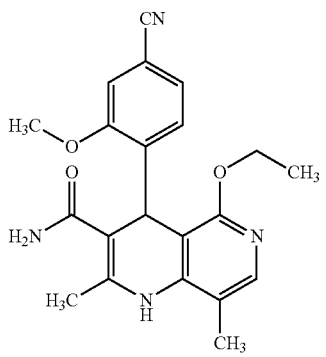
(I)

from the enantiomers 1a or 1b

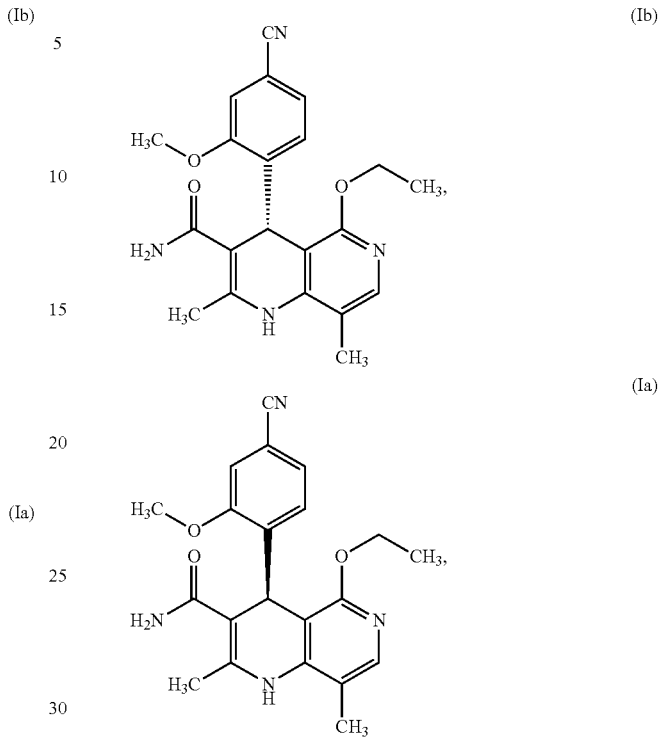

by irradiation with light at a temperature of 0° C. to 100° C. in a suitable solvent, or solvent mixture, selected from the group comprising dichloromethane, acetone, toluene, tetrahydrofuran, methanol, 4-methyl-2-pentanone, methyl ethyl ketone, cyclohexanone, acetonitrile, dimethylformamide, dimethylsulfoxide or mixtures thereof in the concentration range from 0.05% to 10%, and in the presence of a base selected from the group comprising 1,8-diazabicyclo[5.4.0]undec-7-ene, 1,5-diazabicyclo(4.3.0)non-5-ene, triethylamine, diisopropylethylamine, trimethylamine, tripropylamine, tributylamine, 1,4-diazabicyclo(2.2.2)octane, 4-(dimethylamino)pyridine, TBD, 7-methyl-1,5,7-triazabicyclo[4.4.0]dec-5-ene, tetramethylguanidine, N,N,N,N-tetramethyl-1,8-naphthalenediamine, lutidine, pyridine, imidazole, N-methylimidazole and phosphazene, wherein 1-20 equivalents of the organic base are used.

In the context of the present invention, preference is given to a method for preparing racemic (4R,4S)-4-(4-cyano-2-methoxyphenyl)-5-ethoxy-2,8-dimethyl-1,4-dihydro-1,6-naphthyridine-3-carboxamide of the formula (I), from the enantiomers Ia or Ib, by irradiating with light at a temperature from 30° C. to 70° C. in a suitable solvent, or solvent mixture, selected from the group comprising acetone, acetonitrile, dimethylformamide and dimethylsulfoxide or mixtures thereof, in the concentration range of 0.05% to 10%, and in the presence of a base selected from the group comprising 1,8-diazabicyclo[5.4.0]undec-7-ene, 1,5-diazabicyclo(4.3.0)non-5-ene, 1,5,7-triazabicyclo[4.4.0]dec-5-ene and 7-methyl-1,5,7-triazabicyclo[4.4.0]dec-5-ene, wherein 2 to 15 equivalents of the organic base are used.

Particular preference is given in the context of the present invention to a method for preparing racemic (4R,4S)-4-(4-cyano-2-methoxyphenyl)-5-ethoxy-2,8-dimethyl-1,4-dihydro-1,6-naphthyridine-3-carboxamide of the formula (I),

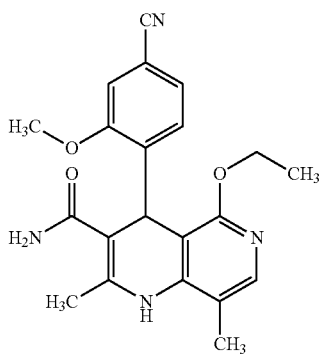

(I)

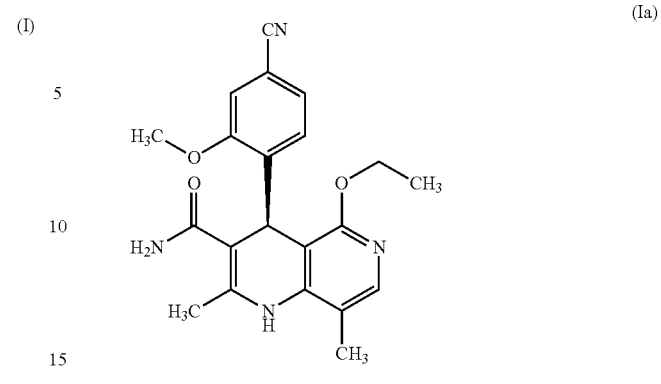

(Ia)

from the enantiomers Ia or Ib

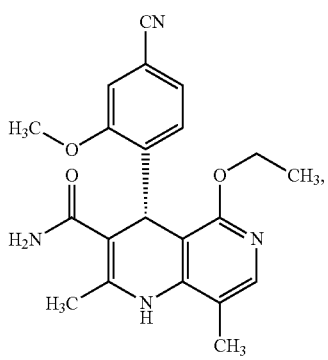

(Ib)

characterized in that a compound of the formula (Ib)

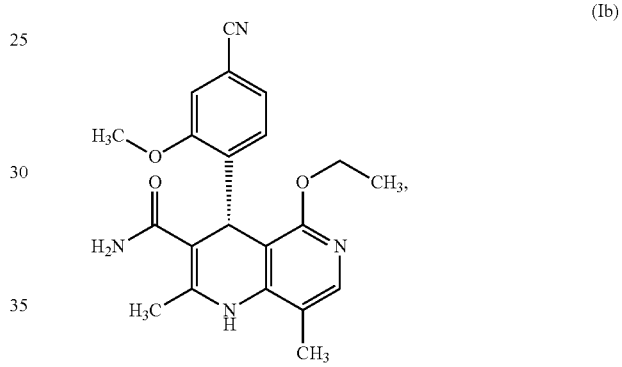

(Ib)

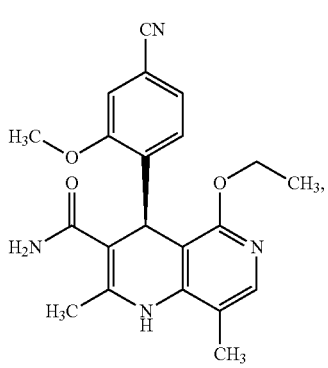

(Ia)

is converted in a suitable solvent, or solvent mixture in the presence of a base by irradiation with light, to a racemic compound of the formula (I)

by irradiation with light at a temperature of 40° C. to 60° C. in acetone or acetonitrile or mixtures thereof in the concentration range of 0.05% to 10%, and in the presence of 1,8-diazabicyclo[5.4.0]undec-7-ene or 1,5-diazabicyclo(4.3.0)non-5-ene, wherein 5-12 equivalents of the organic base are used.

The present invention also relates to a method for preparing (4S)-4-(4-cyano-2-methoxyphenyl)-5-ethoxy-2,8-dimethyl-1,4-dihydro-1,6-naphthyridine-3-carboxamide of the formula (Ia)

(I)

and this racemic compound is converted, by means of optical resolution using a chiral tartaric acid ester of the formula (III)

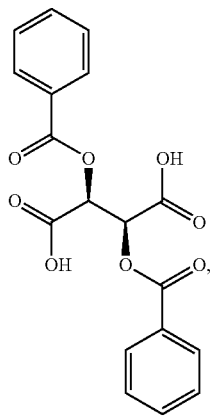

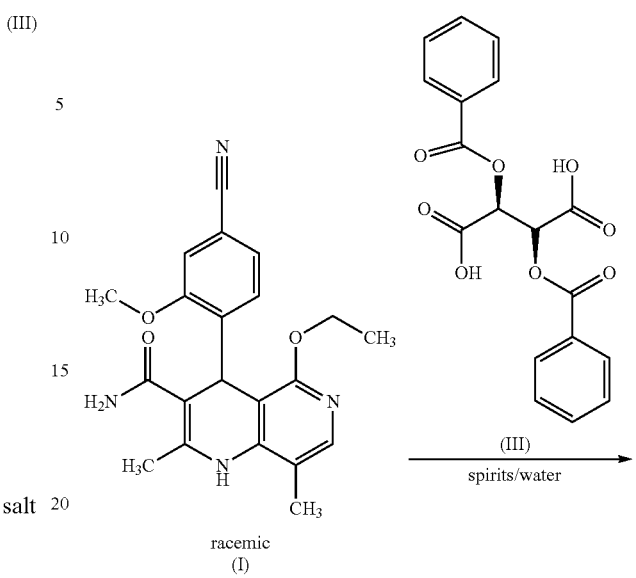

in a spirits/water mixture, firstly to the diastereomeric salt (IVa)

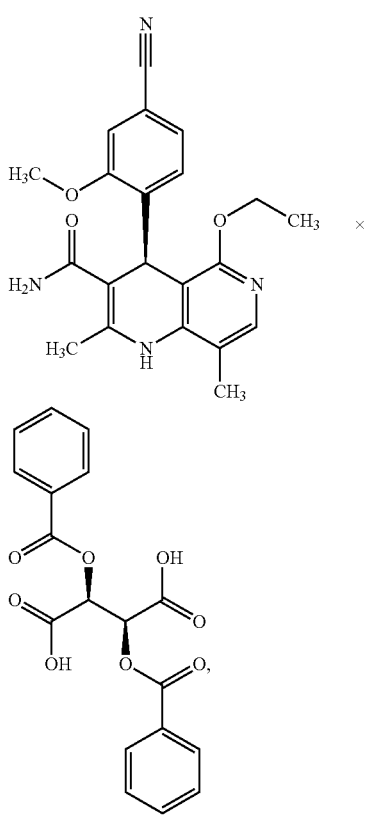

and this is then treated with a base and the solvent removed.

The wrong enantiomer (Ib) may also be obtained by optical resolution, which may be carried out as described below:

In an as yet unpublished method, instead of the irradiation used according to the invention, a tartaric acid ester is used. This method is now described as follows: For operation on an industrial scale, (+)-dibenzoyltartaric acid (III) is used for the optical resolution of (I); both the anhydrous form and the hydrate may be used.

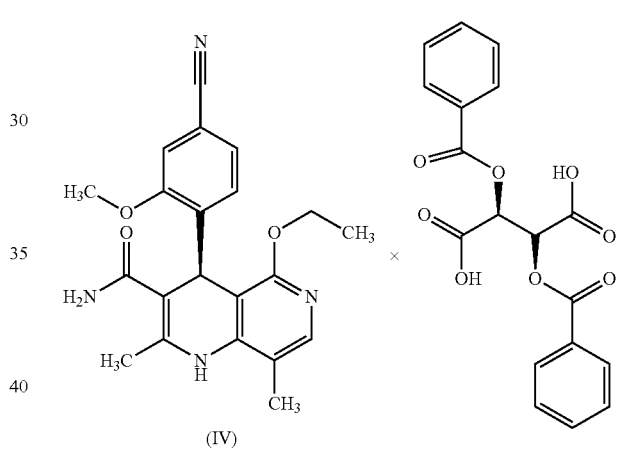

The compound according to formula (IV) in the as yet unpublished method described herein is identical to the compound (Va) of the present invention. The optical resolution is preferably carried out in a spirits/water mixture. The wrong enantiomer (Ib) remains in the mother liquor in this case and may be isolated for recycling.

The subsequent release of finerenone (Ia, crude),

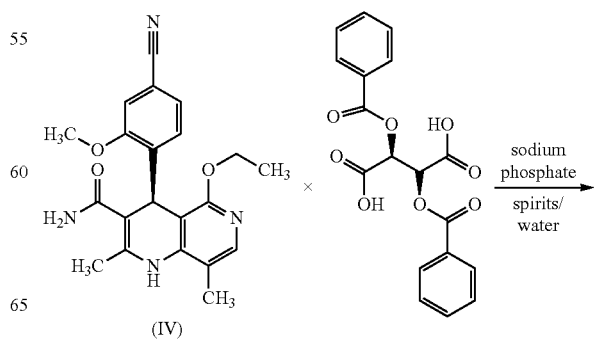

-continued

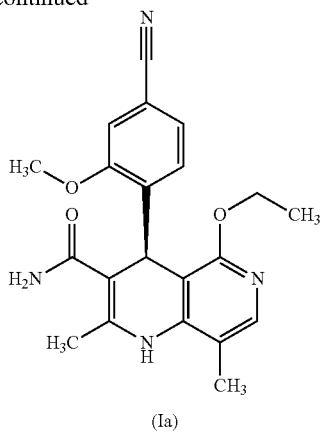

(Ia)

is preferably carried out in a spirits/water mixture using sodium phosphate as base. In cases requiring reprocessing, if the proportion of (+)-dibenzoyltartaric acid (III) is >0.1%,

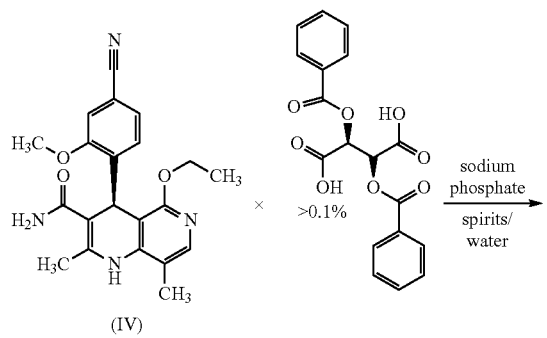

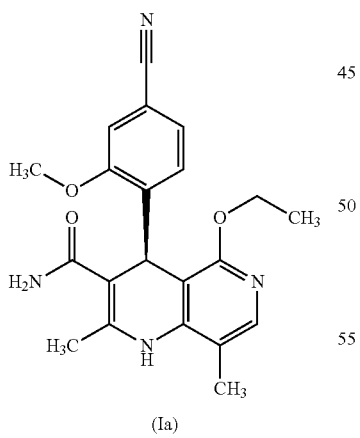

(Ia)

reprocessing is preferably carried out in a spirits/water mixture using sodium phosphate as base. Final crystallization to afford pure finerenone (Ia) is preferably carried out using spirits as solvent.

The wrong enantiomer (Ib) is isolated from the mother liquor by adjusting the combined mother liquor and wash solutions to pH=7.5 by adding an aqueous sodium phosphate solution at room temperature. Under reduced pressure (85 to 65 mbar, internal temperature 38° to 20° C.), the spirits are then substantially distilled off and the mixture is reduced to a defined end volume. The mixture is cooled to room temperature and the precipitated suspension is stirred at 20°-22° C. The suspension was filtered off and washed twice with water. The wet product was dried at 50° C. overnight (ca. 16 h) under reduced pressure (<100 mbar). Yields of (Ib) are generally >80% of theory, based on the racemate (I) used.

For economic reasons, there was a need not to destroy this enantiomer of the formula (Ib), but to invent a process which enables conversion of the compound of the formula (Ib) to a racemic mixture of the formula (I), in order to subject it to another enantiomer separation by means of SMB or to an optical resolution, for example using (+)-dibenzoyltartaric acid, as described above.

In contrast to this racemization using a tartaric acid ester, irradiation is carried out in the present method according to the invention. It has now been found that, surprisingly, this is achieved by irradiating the wrong enantiomer (Ib) with light in a solvent, or solvent mixture, in the presence of a base, and in the presence of oxygen.

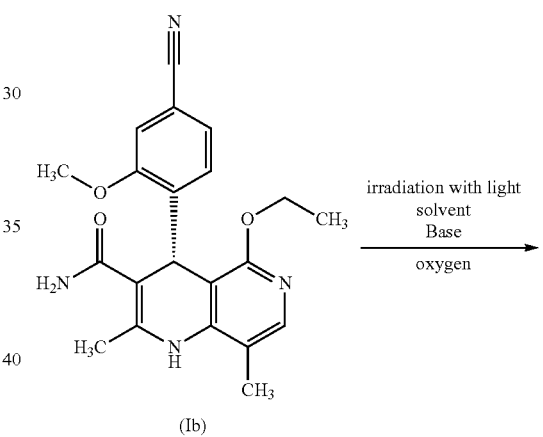

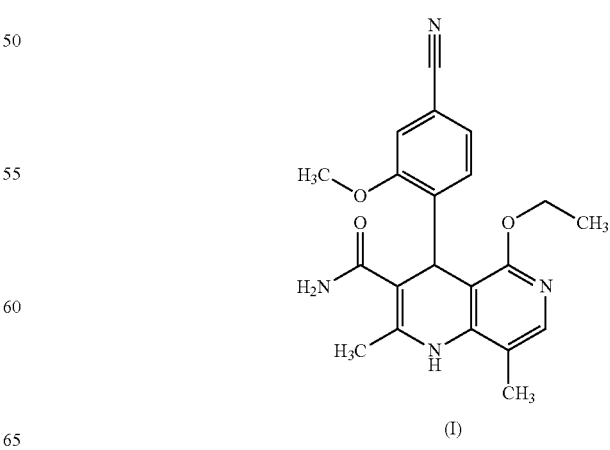

The same also succeeds by converting finerenone (Ia):

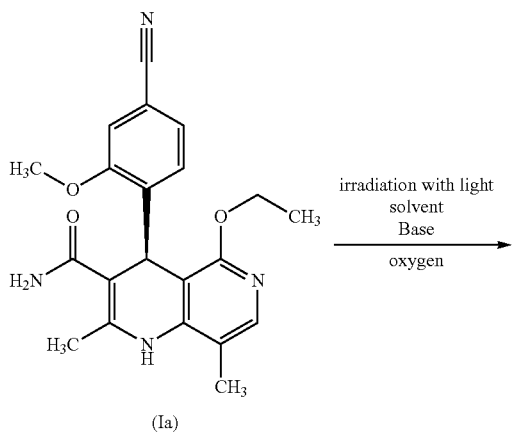

(Ia)

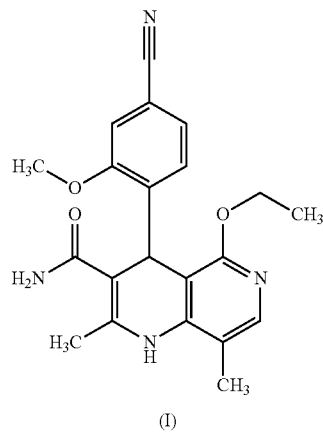

(I)

The attempt to directly racemize the compound of the formula (Ib), by treating for example compound (Ib) with strong bases or acids, was unsuccessful. The reaction with transition metal complexes such as palladium and iridium catalysts also did not result in the desired outcome.

An electrochemical two-stage process has been described in the prior art (WO 2017032678 A1) in which firstly a chemical or electrochemical oxidation to the pyridine takes place (aromatization of the dihydropyridine) and then an electrochemical reduction. A disadvantage of the electrochemical process is that said process has to be carried out in three stages. Thus, the direct oxidation (chemical or electrochemical) of the wrong enantiomer (Ib) affords an optically enriched pyridine derivative (II) (due to atropisomerism),

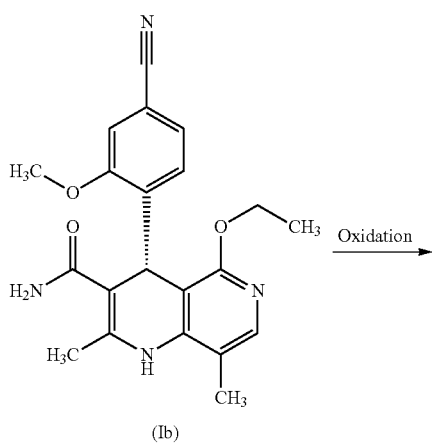

(Ib)

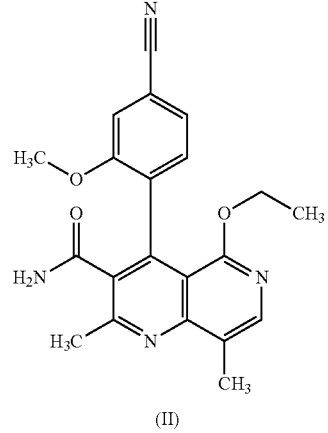

(II)

which in a second step is equilibrated to the racemate by thermal treatment and is then reduced in a third step to the racemate (I).

There is extensive literature about the photochemistry of dihydropyridine derivates, for example in H Freytag, W. Neudert, J. Prakt. Chem. 1932, 135, 15; H. Freytag, F. Hlucka, J. Prakt. Chem. 1932, 135, 288; H. Freytag, J. Prakt. Chem. 1934, 139, 44; J. Joussot-Dubien, J. Houdard, Tetrahedron Let. 1967, 44, 4389-4391; Koizumi, Bull. Chem. SOC. Jap. 1966, 39, 1221; Koizumi, Bull. Chem. SOC. Jap. 1967, 40, 2486; Koizumi, Bull. Chem. SOC. Jap. 1968, 41, 1056; D. G. Whitten, Y. J. Lee, J. Am. Chem. Soc. 1971, 93, 961-966; T. J. van Bergen, R. M. Kellogg, J. Am. Chem. Soc 1972, 94, 8451-8471; R. Leuschner, J. K. Dohrmann, Journal of Photochemistry 1986, 33, 321-331; D. G. Whitte, Y. J. Lee, J. Am. Chem. Soc 1971, 93, 961-966; T. J. van Bergen, R. M. Kellogg, J. Am. Chem. Soc 1972, 94, 8451-8471; T. J. van Bergen, R. M. Kellogg, J. Am. Chem. Soc 1972, 94, 8451-8471; R. Leuschner, J. K. Dohrmann, Journal of Photochemistry 1986, 33, 321-331; T. J. van Bergen, R. M. Kellogg, J. Am. Chem. Soc 1972, 94, 8451-8471; Jacques Joussot-Dubien, Josette Houdard, Tetrahedron Letters, Volume 8, Issue 44, 1967, S. 4389-4391; Journal of Magnetic Resonance (1969), Volume 27, Issue 3, September 1977, pp. 371-384; Tetrahedron, Volume 28, Issue 24, 1972, pp. 5911-5921; R. Leuschner, K. Dohrmann, Journal of Photochemistry, Volume 33, Issue 3, June 1986, pp. 321-331; Junko Shibuya, Mami Nabeshima, Hajime Nagano and Koko Maeda J. Chem. Soc., Perkin Trans. 2, 1988, 1607-1612; Zhong-Li Liu Chem. Commun., 1998, 2451-2452; Al-Jalal, Molecules. 2016 Jun. 30; 21(7); T. J. Van Bergen and Richard M. Kellogg, Journal of the American Chemical Society 1972 94 (24), 8451-8471; Tetrahedron Letters, Volume 10, Issue 59, 1969, Pages 5211-5214; Molecules 2016, 21, 866; Hindawi Publishing Corporation International Journal of Photochemistry Volume 2014, Article ID 176989, 4 pages, http://dx.doi.org/10.1155/2014/176989; Photochemistry and Photobiology, 2007, 83, 722-729; J. Org. Chem., 2006, 71 (5), pp 2037-2045; Monatshefte fir Chemie 2002, 133, 661; International Journal of Photoenergy 2015, Article ID 454895.

Direct racemization by irradiation with light, which is novel in the method according to the invention, and is as yet unknown in the case of chiral dihydropyridine derivatives.

There was therefore a high demand, instead of 3 process steps (as in the case of electrochemistry), to achieve a simplified method which, under mild conditions (light), leads directly to racemization of the wrong enantiomer (Ib)

and thus to the racemate (I). This is achieved with the present novel inventive method.

It was surprising to those skilled in the art that the wrong enantiomer (Ib), and finerenone (Ia) cannot be isomerized by reaction with a strong base, i.e. racemization is not possible. In a surprising manner, this only succeeds, as has been found in the method according to the invention, by the combination of base, irradiation with light and selection of a suitable solvent in the presence of oxygen.

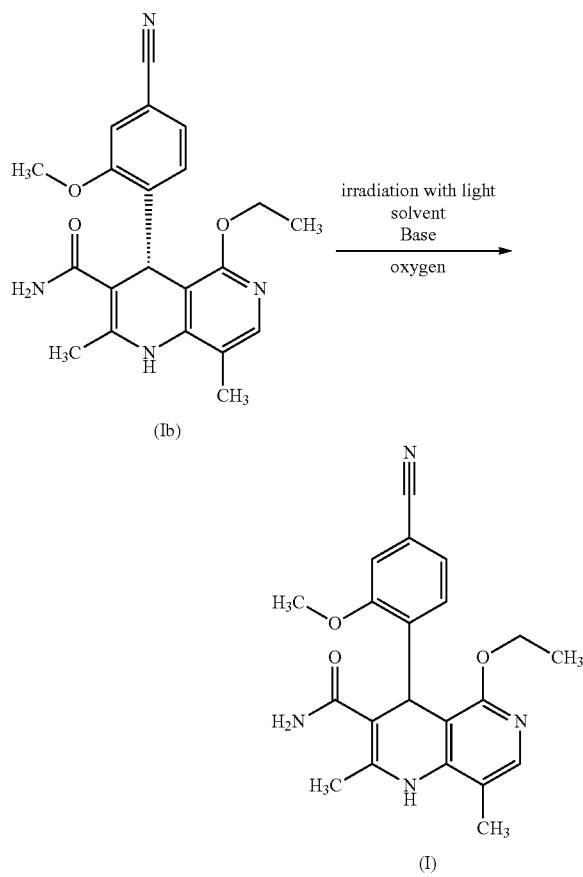

Organic bases have been shown to be particularly suitable, particularly worthy of mention here being 1,8-diazabicyclo[5.4.0]undec-7-ene, 1,5-diazabicyclo(4.3.0)non-5-ene, triethylamine, diisopropylethylamine, trimethylamine, tripropylamine, tributylamine, 1,4-diazabicyclo(2.2.2)octane, 4-(dimethylamino)pyridine, 1,5,7-triazabicyclo[4.4.0] dec-5-ene, 7-methyl-1,5,7-triazabicyclo[4.4.0]dec-5-ene, tetramethylguanidine, N,N,N,N-tetramethyl-1,8-naphthalenediamine, lutidine, pyridine, imidazole, N-methylimidazole, phosphazene. Particular preference is given to 1,8-diazabicyclo[5.4.0]undec-7-ene, 1,5-diazabicyclo(4.3.0) non-5-ene and 1,5,7-triazabicyclo[4.4.0]dec-5-ene and 7-methyl-1,5,7-triazabicyclo[4.4.0]dec-5-ene, very particular preference being given to 1,8-diazabicyclo[5.4.0]undec-7-ene and 1,5-diazabicyclo(4.3.0)non-5-ene.

1 to 20 equivalents of an organic base are used, preferably 2 to 15 equivalents, particularly preferably 5 to 12 equivalents.

Suitable solvents for the photochemical reaction are dichloromethane, acetone, toluene, tetrahydrofuran, methanol, 4-methyl-2-pentanone, methyl ethyl ketone, cyclohexanone, acetonitrile, dimethylformamide, dimethylsulfoxide or mixtures thereof such as acetone/methanol, acetone/methanol, acetone/tetrahydrofuran. Particular preference is given to acetone, acetonitrile, dimethylformamide and dimethylsulfoxide. Very particular preference is given to acetone and acetonitrile. The operation is in the concentration range of 0.05% to 10%, depending on the solvent. Here, for example, if reference is made to a concentration range of 0.05%, this means that 0.05 g is dissolved in 100 mL.

The irradiation is conducted at 0° C. to 100° C., depending on the solvent. A preferred temperature range is however 30° to 70° C. Preference is given to 40° to 60° C.

The irradiation time is 1 h to 40 h and also depends heavily on the solvent used and the base.

In some cases, depending on the solvent selected, the optional addition of photosensitizers may be of advantage. For this purpose, anthracene, rose bengal, eosin Y, DMPA, benzoquinone, benzophenone, acetophenone, fluorene, xanthone, benzene, N-bromosuccinimide, Ru(bpy)3, or Ruporphyrin may be used.

It is possible to use Hg lamps and also LEDS as radiation sources. The use of UV filters has proven to be advantageous, particularly Duran filters (with cut-off <300 nm) UV filter from 282 nm have proven to be effective.

The reaction can be conducted in batchwise mode or also as a flow process depending on the batch size.

The photochemical racemisation proceeds as a one-pot reaction in which, in the first phase of the irradiation, synthetic air is passed into the mixture within 0.5 h-5 h. Alternatively, synthetic air may be introduced initially without irradiation; if air is introduced without irradiation, irradiation is subsequently carried out for 0.5 h-5 h. For the second component step of the one-pot reaction, irradiation is again subsequently carried out under inert conditions (displacement of traces of oxygen by introducing nitrogen or argon). The reaction may be monitored by sample removal and checking the respective optical purity.

At the end of the reaction, the work-up and isolation of the desired racemate (I) is carried out as follows: Firstly, the solvent is distilled off at standard pressure or under reduced pressure up to a certain volume and a certain amount of water is added (for the ratios by amount see examples). The ratios by amount are varied depending on the solvent or solvent mixture used. Racemate (I) precipitates in this case and is then isolated by filtration over a filter or by centrifugation and is then dried. Drying is preferably effected at reduced pressure at temperatures of 40°-80° C. Depending on the quality, the products obtained may be directly further processed (SMB separation or optical resolution using dibenzoyltartaric acid are carried out). However, a final crystallization for end purification may also be carried out once again. Suitable solvents for this purpose are ethanol, isopropanol, methanol, acetonitrile and tetrahydrofuran, also each in combination with water.

Starting from the wrong enantiomer (Ib), yields of the racemate (I) achieved are from: 50%-75% of theory. The chemical purities are very high, it being possible to obtain purities of up to 99.1% (HPLC, area). The enantiomeric excess is <1-2%. A racemate (I) thus obtained may be successfully used in a subsequent racemate resolution method, be it an SMB or optical resolution using dibenzoyltartaric acid, and corresponds to the demands of the required specifications with respect to purity and enantiomeric excess.

In addition to the method described above, the direct conversion of (Ib) to (I) in a one-pot process, it has surprisingly been found that a photochemical reduction by irradiation with light in a suitable solvent, or solvent mixture, and in the presence of a base, of the corresponding pyridine compound (II), which is obtained by chemical or electrochemical oxidation starting from racemic or else optically enriched compounds (see WO 2017032678 A1), affords compound (I) in racemic form

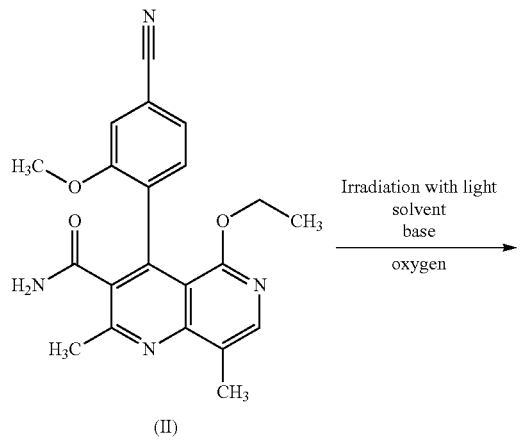

(II)

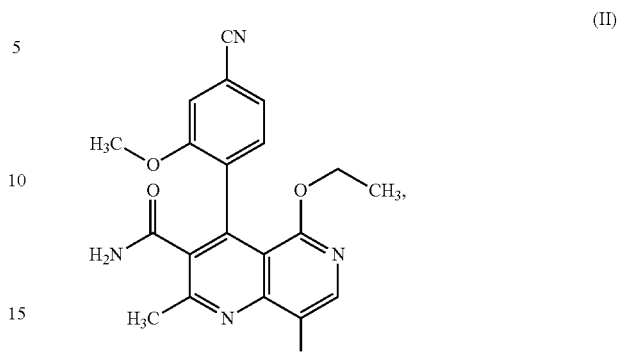

(II)

by irradiation with light in a suitable solvent, or solvent mixture, and in the presence of a base.

Preference is given in the context of the present invention to a method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

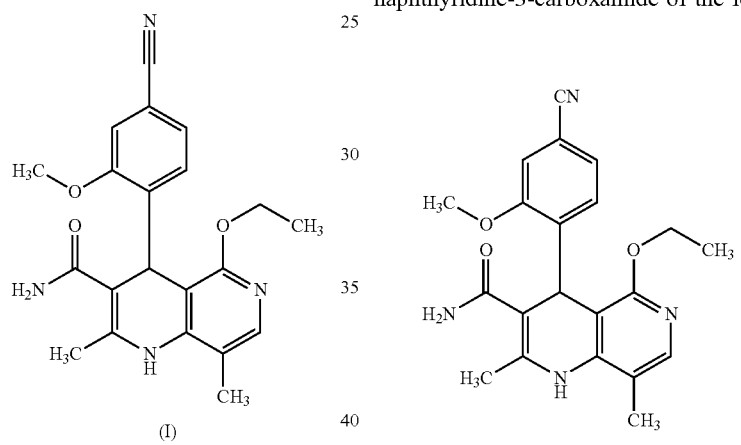

(I)

The present invention also relates to a novel method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

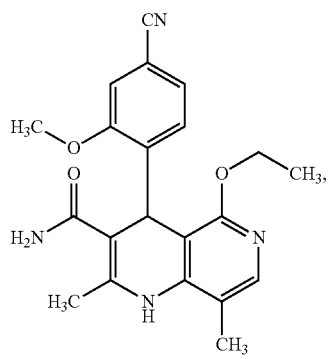

(I)

from the pyridine of the formula II

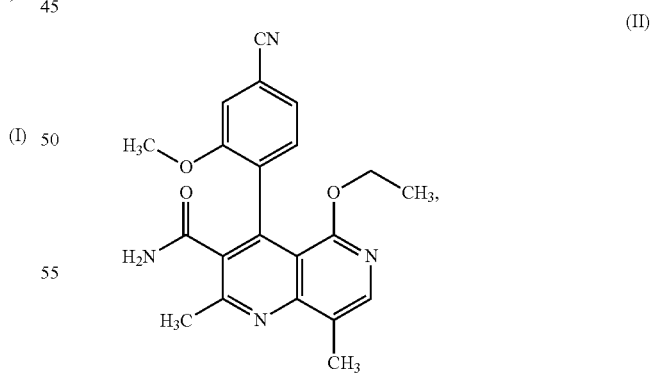

(II)

by irradiation with light at a temperature of 0° C. to 100° C. in a suitable solvent, or solvent mixture, selected from the group comprising dichloromethane, acetone, toluene, tetrahydrofuran, methanol, 4-methyl-2-pentanone, methyl ethyl ketone, cyclohexanone, acetonitrile, dimethylformamide, dimethylsulfoxide or mixtures thereof in the concentration range from 0.05% to 10%, and in the presence of a base selected from the group comprising 1,8-diazabicyclo[5.4.0]undec-7-ene, 1,5-diazabicyclo(4.3.0)non-5-ene, triethylamine, diisopropylethylamine, trimethylamine, tripropylamine, tributylamine, 1,4-diazabicyclo(2.2.2)octane, 4-(dimethylamino)pyridine, 1,5,7-triazabicyclo[4.4.0]dec-5-ene, 7-methyl-1,5,7-triazabicyclo[4.4.0]dec-5-ene, tetramethylguanidine, N,N,N,N-tetramethyl-1,8-naphthalenediamine, lutidine, pyridine, imidazole, N-methylimidazole and phosphazene, wherein 1-20 equivalents of the organic base are used.

In the context of the present invention, preference is given to a method for preparing racemic (4R,4S)-4-(4-cyano-2-methoxyphenyl)-5-ethoxy-2,8-dimethyl-1,4-dihydro-1,6-naphthyridine-3-carboxamide of the formula (I), from the pyridine of the formula II, by irradiating with light at a temperature from 30° C. to 70° C. in a suitable solvent, or solvent mixture, selected from the group comprising acetone, acetonitrile, dimethylformamide and dimethylsulfoxide or mixtures thereof, in the concentration range of 0.05% to 10%, and in the presence of a base selected from the group comprising 1,8-diazabicyclo[5.4.0]undec-7-ene, 1,5-diazabicyclo(4.3.0)non-5-ene, 1,5,7-triazabicyclo[4.4.0]dec-5-ene and 7-methyl-1,5,7-triazabicyclo[4.4.0]dec-5-ene, wherein 2 to 15 equivalents of the organic base are used.

Particular preference is given in the context of the present invention to a method for preparing racemic (4R,4S)-4-(4-cyano-2-methoxyphenyl)-5-ethoxy-2,8-dimethyl-1,4-dihydro-1,6-naphthyridine-3-carboxamide of the formula (I),

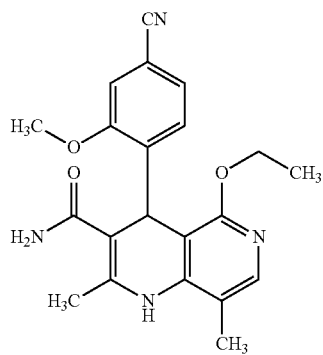

(I)

from the pyridine of the formula (II)

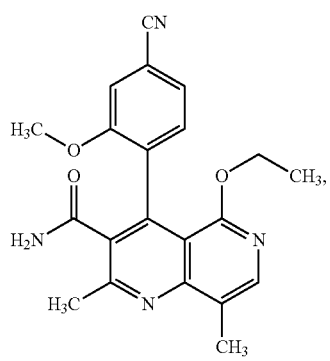

(II)

by irradiation with light at a temperature of 40° C. to 60° C. in acetone or acetonitrile or mixtures thereof in the concentration range of 0.05% to 10%, and in the presence of 1,8-diazabicyclo[5.4.0]undec-7-ene or 1,5-diazabicyclo(4.3.0)non-5-ene, wherein 5-12 equivalents of the organic base are used.

Organic bases have been shown to be particularly suitable, particularly worthy of mention here being 8-diazabicyclo[5.4.0]undec-7-ene, 1,5-diazabicyclo(4.3.0)non-5-ene, triethylamine, diisopropylethylamine, trimethylamine, tripropylamine, tributylamine, 1,4-diazabicyclo(2.2.2)octane, 4-(dimethylamino)pyridine, 1,5,7-triazabicyclo[4.4.0]dec-5-ene, 7-methyl-1,5,7-triazabicyclo[4.4.0]dec-5-ene, tetramethylguanidine, N,N,N,N-tetramethyl-1,8-naphthalenediamine, lutidine, pyridine, imidazole, N-methylimidazole, phosphazene. Particular preference is given to 1,8-diazabicyclo[5.4.0]undec-7-ene, 1,5-diazabicyclo(4.3.0)non-5-ene and 1,5,7-triazabicyclo[4.4.0]dec-5-ene and 7-methyl-1,5,7-triazabicyclo[4.4.0]dec-5-ene, very particular preference being given to 1,8-diazabicyclo[5.4.0]undec-7-ene and 1,5-diazabicyclo(4.3.0)non-5-ene.

1-20 equivalents of an organic base are used, preferably 2-15 equivalents, particularly preferably 5-12 equivalents.

Suitable solvents for the photochemical reaction are dichloromethane, acetone, toluene, tetrahydrofuran, methanol, 4-methyl-2-pentanone, methyl ethyl ketone, cyclohexanone, acetonitrile, dimethylformamide, dimethylsulfoxide or mixtures thereof such as acetone/methanol, acetone/methanol, acetone/tetrahydrofuran. Particular preference is given to acetone, acetonitrile, dimethylformamide and dimethylsulfoxide. Very particular preference is given to acetone and acetonitrile. The operation is in the concentration range of 0.05% to 10%, depending on the solvent.

The irradiation is conducted at 0° C. to 100° C., depending on the solvent. A preferred temperature range is however 300-70° C.

The irradiation time is 1 hour to 40 hours and also depends heavily on the solvent used and the base, preferably 10 hours-20 hours. In one embodiment, the irradiation is effected for 6 to 40 hours. In one embodiment, the irradiation time is 6 to 35 hours. In one embodiment, the irradiation time is 6 to 20 hours. In one embodiment, the irradiation time is 6 to 15 hours. In one embodiment, the irradiation time is 6 to 10 hours. In one embodiment, the irradiation time is 6 to 9 hours. In one embodiment, the irradiation time is 8 to 20 hours. In one embodiment, the irradiation time is 6 to 34 hours.

In some cases, depending on the solvent selected, the optional addition of photosensitizers may be of advantage. For this purpose, anthracene, rose bengal, eosin Y, DMPA, benzoquinone, benzophenone, acetophenone, fluorene, xanthone, benzene, N-bromosuccinimide, Ru(bpy)3, or Ru-porphyrin may be used.

It is possible to use mercury lamps and also LEDS as radiation sources. The utilization of UV filters has been used as advantageous, particularly Duran filter (with cut-off <300 nm) UV filters from 282 nm have proven to be effective.

The reaction can be conducted in batchwise mode or also as a flow process depending on the batch size.

At the end of the reaction, the work-up and isolation of the desired racemate (I) is carried out as follows: The solvent is distilled off at standard pressure or under reduced pressure up to a certain volume and a certain amount of water is added (for the ratios by amount see examples). The ratios by amount are varied depending on the solvent or solvent mixture used. The product precipitates in this case and may then be isolated by filtration over a filter or by centrifugation and is then dried. Drying is preferably effected at reduced pressure at temperatures of 300-80° C. Preferably at 40°-60° C. Depending on the quality, the products obtained may be directly further processed (SMB separation or optical resolution using dibenzoyltartaric acid are carried out). However, a final crystallization for end purification may also be carried out once again. Suitable solvents for this purpose are ethanol, isopropanol, methanol, acetonitrile and tetrahydrofuran, also each in combination with water.

Starting from the pyridine derivative (II), yields of 60%-90% of theory of the racemate (I) are achieved. The chemical purities are very high, it being possible to obtain purities of up to >95% (HPLC, area). The enantiomeric excess is <1-2%. A material thus obtained may be successfully used in a subsequent racemate resolution method, be it an SMB or optical resolution using dibenzoyltartaric acid, and corresponds to the demands of the required specifications with respect to purity and enantiomeric excess.

In addition to this novel method starting from pyridine derivative (II), particular preference is given however to the one-pot method starting from (Ib).

The novel method according to the invention is characterized by high efficiency with respect to yield and chemical purity. The method is environmentally friendly since light is used as the actual "reagent". The method is scalable up to an industrial scale, since photoreactors in the flow process have been used in industry for a long time, that is to say no special equipment is needed in contrast to electrochemistry. Therefore, this novel inventive method exhibits enormous economic advantages compared to the prior art.

Paragraphs 1. to 9.

In the following paragraphs 1. to 9., further embodiments of the invention are described:

1. Method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

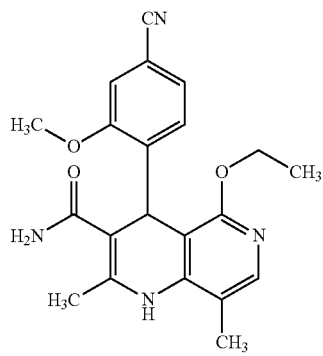

(I)

from the enantiomers Ia or Ib

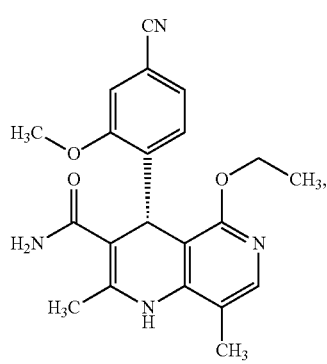

(Ib)

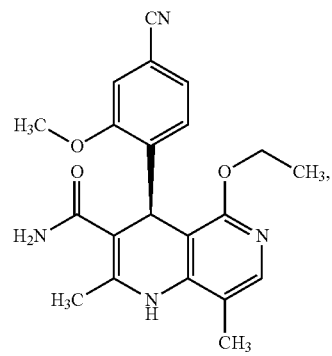

(Ia)

by irradiation with light in a suitable solvent, or solvent mixture, and in the presence of a base.

2. Method according to paragraph 1 for preparing racemic (4R,4S)-4-(4-cyano-2-methoxyphenyl)-5-ethoxy-2,8-dimethyl-1,4-dihydro-1,6-naphthyridine-3-carboxamide of the formula (I)

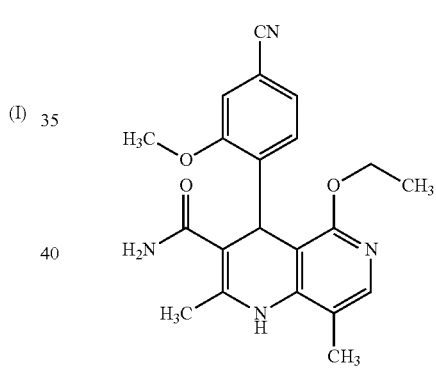

(I)

from the enantiomers Ia or Ib

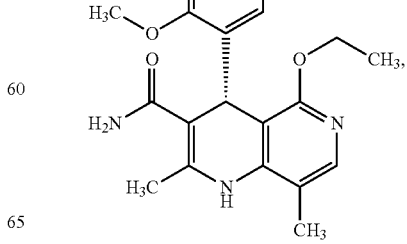

(Ib)

-continued

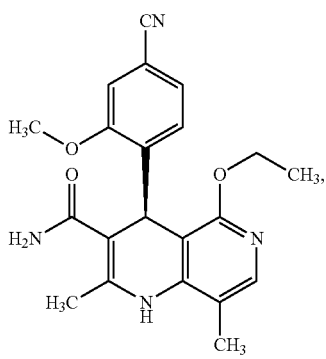
(Ia)

by irradiation with light at a temperature of 0° C. to 100° C. in a suitable solvent, or solvent mixture, selected from the group comprising dichloromethane, acetone, toluene, tetrahydrofuran, methanol, 4-methyl-2-pentanone, methyl ethyl ketone, cyclohexanone, acetonitrile, dimethylformamide, dimethylsulfoxide or mixtures thereof in the concentration range from 0.05% to 10%, and in the presence of a base selected from the group comprising 1,8-diazabicyclo[5.4.0]undec-7-ene, 1,5-diazabicyclo(4.3.0)non-5-ene, triethylamine, diisopropylethylamine, trimethylamine, tripropylamine, tributylamine, 1,4-diazabicyclo(2.2.2)octane, 4-(dimethylamino)pyridine, 1,5,7-triazabicyclo[4.4.0]dec-5-ene, 7-methyl-1,5,7-triazabicyclo[4.4.0]dec-5-ene, tetramethylguanidine, N,N,N,N-tetramethyl-1,8-naphthalenediamine, lutidine, pyridine, imidazole, N-methylimidazole and phosphazene, wherein 1-20 equivalents of the organic base are used.

3. Method according to paragraph 1 or 2 for preparing racemic (4R,4S)-4-(4-cyano-2-methoxyphenyl)-5-ethoxy-2,8-dimethyl-1,4-dihydro-1,6-naphthyridine-3-carboxamide of the formula (I), from the enantiomers Ia or Ib, by irradiating with light at a temperature from 30° C. to 70° C. in a suitable solvent, or solvent mixture, selected from the group comprising acetone, acetonitrile, dimethylformamide and dimethylsulfoxide or mixtures thereof, in the concentration range of 0.05% to 10%, and in the presence of a base selected from the group comprising 1,8-diazabicyclo[5.4.0]undec-7-ene, 1,5-diazabicyclo(4.3.0)non-5-ene, 1,5,7-triazabicyclo[4.4.0]dec-5-ene and 7-methyl-1,5,7-triazabicyclo[4.4.0]dec-5-ene, wherein 2 to 15 equivalents of the organic base are used.

4. Method according to paragraph 1, 2 or 3 for preparing racemic (4R,4S)-4-(4-cyano-2-methoxyphenyl)-5-ethoxy-2,8-dimethyl-1,4-dihydro-1,6-naphthyridine-3-carboxamide of the formula (I), (I)

from the enantiomers Ia or Ib

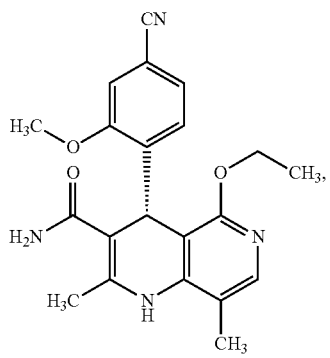
(Ib)

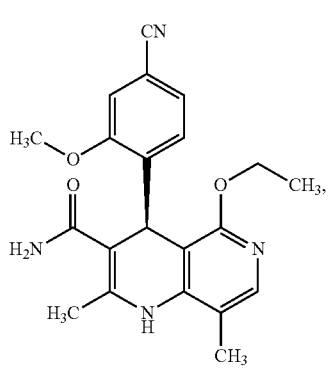
(Ia)

by irradiation with light at a temperature of 40° C. to 60° C. in acetone or acetonitrile or mixtures thereof in the concentration range of 0.05% to 10%, and in the presence of 1,8-diazabicyclo[5.4.0]undec-7-ene or 1,5-diazabicyclo(4.3.0)non-5-ene, wherein 5-12 equivalents of the organic base are used.

5. Method for preparing (4S)-4-(4-cyano-2-methoxyphenyl)-5-ethoxy-2,8-dimethyl-1,4-dihydro-1,6-naphthyridine-3-carboxamide (Ia)

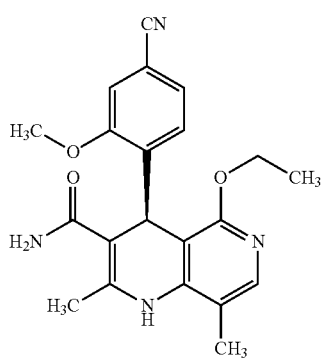
(Ia)

characterized in that a compound of the formula (Ib)

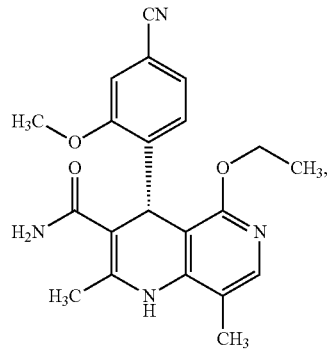

(Ib)

is converted in a suitable solvent, or solvent mixture at a temperature of 0° C. to 100° C. in the presence of a base by irradiation with light, to a racemic compound of the formula (I)

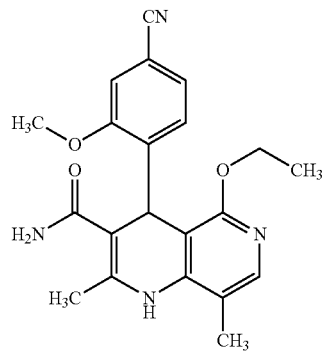

(I)

and this racemic compound is converted, by means of optical resolution using a chiral tartaric acid ester of the formula (III)

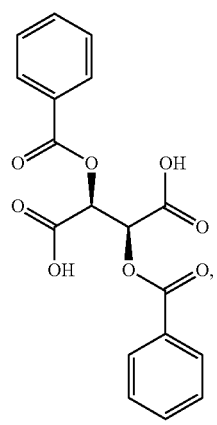

(III)

in a spirits/water mixture, firstly to the diastereomeric salt (IVa)

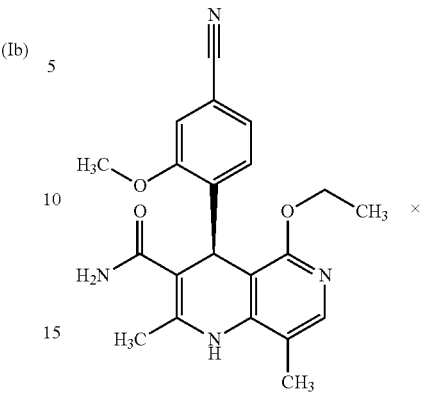

(IVa)

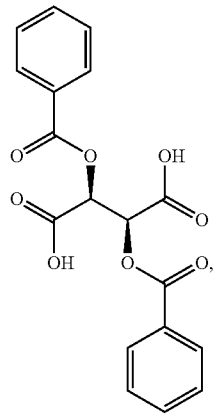

and this is then treated with a base and the solvent removed.

6. Method according to paragraph 5 for preparing (4S)-4-(4-cyano-2-methoxyphenyl)-5-ethoxy-2,8-dimethyl-1,4-dihydro-1,6-naphthyridine-3-carboxamide of the formula (Ia)

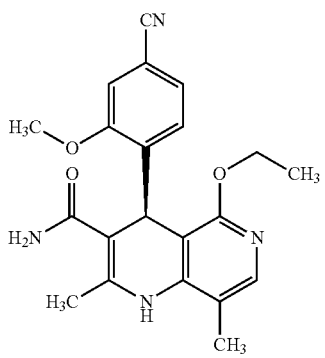

(Ia)

characterized in that a compound of the formula (Ib)

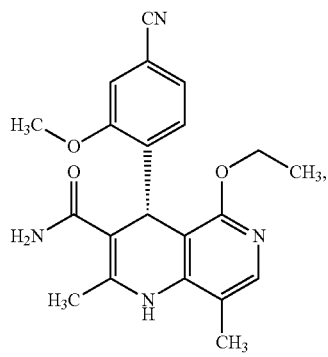
(Ib)

by irradiation with light at a temperature of 30° C. to 70° C. in a suitable solvent, or solvent mixture, selected from the group comprising acetone, acetonitrile, dimethylformamide and dimethylsulfoxide or mixtures thereof, in the concentration range of 0.05% to 10%, and in the presence of a base selected from the group comprising 1,8-diazabicyclo[5.4.0]undec-7-ene, 1,5-diazabicyclo(4.3.0)non-5-ene, 1,5,7-triazabicyclo[4.4.0]dec-5-ene and 7-methyl-1,5,7-triazabicyclo[4.4.0]dec-5-ene, wherein 2-15 equivalents of the organic base are used,
is converted to a racemic compound of the formula (I)

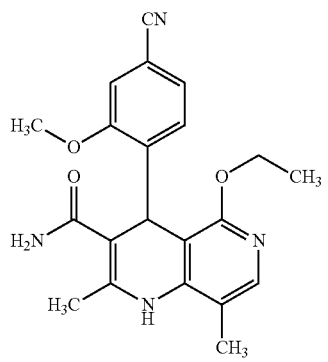
(I)

and this racemic compound is converted, by means of optical resolution using a chiral tartaric acid ester of the formula (III)

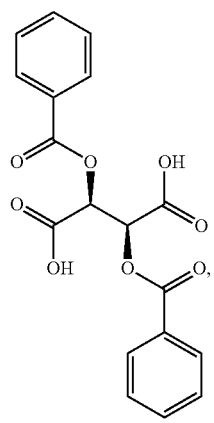
(III)

in a spirits/water mixture, firstly to the diastereomeric salt (IVa)

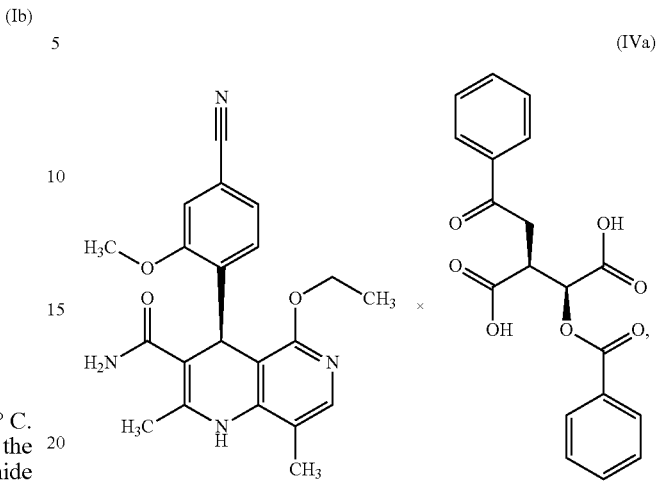
(IVa)

and this is then treated with sodium phosphate and the solvent removed.

7. Method according to paragraph 5 or 6 for preparing (4S)-4-(4-cyano-2-methoxyphenyl)-5-ethoxy-2,8-dimethyl-1,4-dihydro-1,6-naphthyridine-3-carboxamide (Ia)

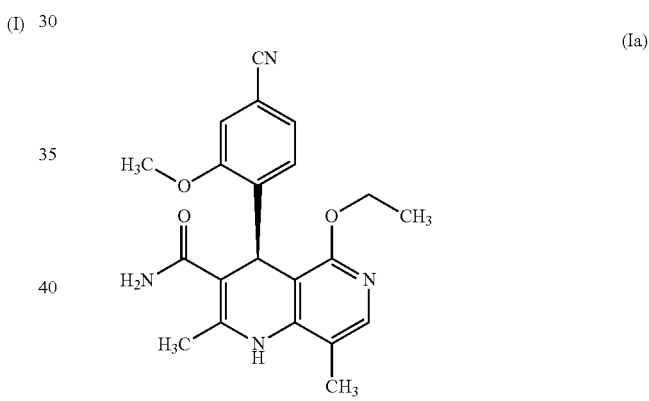
(Ia)

characterized in that a compound of the formula (Ib)

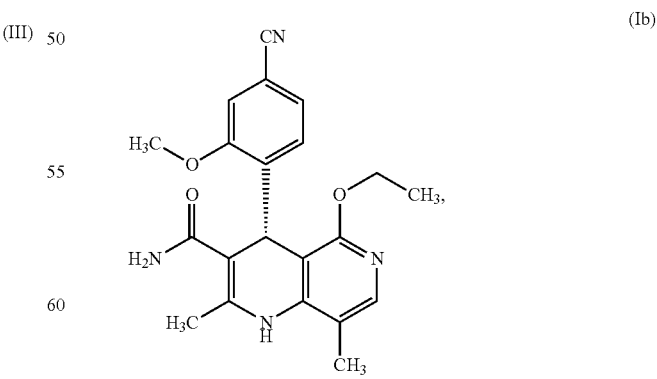
(Ib)

at a temperature of 40° C. to 60° C. in acetone or acetonitrile or mixtures thereof in the concentration range of 0.05% to 10%, and in the presence of 1,8-diazabicyclo[5.4.0]undec- 7-ene or 1,5-diazabicyclo(4.3.0)non-5-ene, wherein 5-12 equivalents of the organic base are used, is converted by irradiation with light to a racemic compound of the formula (I)

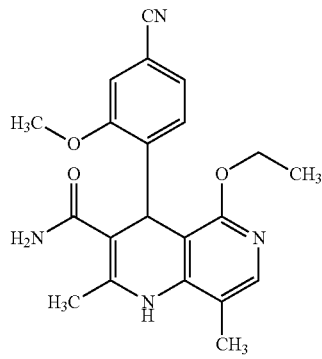

and this racemic compound is converted, by means of optical resolution using a chiral tartaric acid ester of the formula (III)

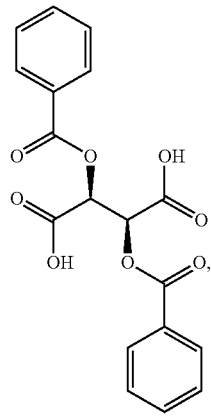

in a spirits/water mixture, firstly to the diastereomeric salt (IVa)

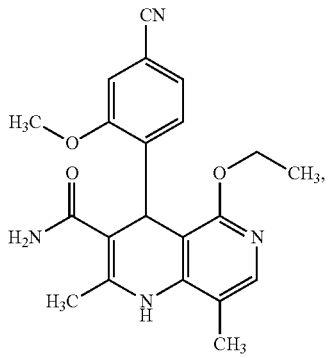

and this is then treated with sodium phosphate and the solvent removed.

8. Method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

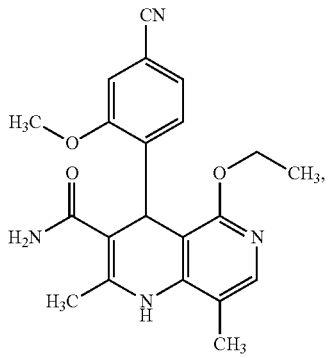

from the pyridine of the formula (II)

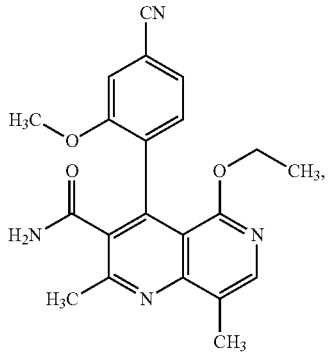

by irradiation with light in a suitable solvent, or solvent mixture, and in the presence of a base.

9. Method according to paragraph 8 for preparing racemic (4R,4S)-4-(4-cyano-2-methoxyphenyl)-5-ethoxy-2,8-dimethyl-1,4-dihydro-1,6-naphthyridine-3-carboxamide of the formula (I)

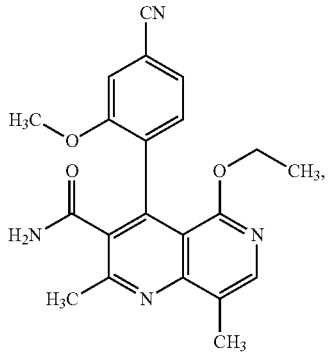

from the pyridine of the formula (II)

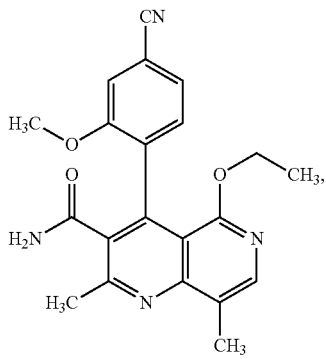

(II)

by irradiation with light at a temperature of 40° C. to 60° C. in acetone or acetonitrile or mixtures thereof in the concentration range of 0.05% to 10%, and in the presence of 1,8-diazabicyclo[5.4.0]undec-7-ene or 1,5-diazabicyclo(4.3.0)non-5-ene, wherein 5-12 equivalents of the organic base are used.

Paragraphs (1) to (42)

In the following paragraphs (1) to (28), further embodiments of the invention are described:

(1) Method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

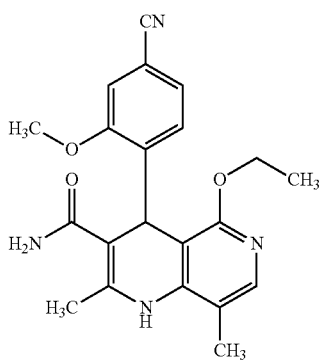

(I)

from the enantiomers of the formulae (Ia) and/or (Ib)

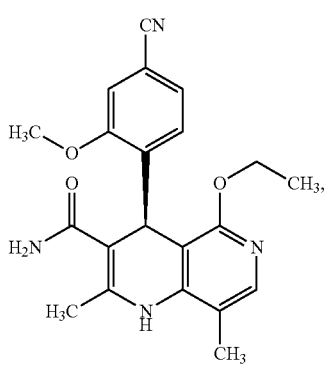

(Ia)

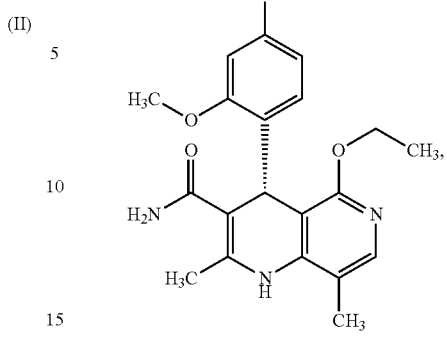

(Ib)

comprising the step of (i):
(i) irradiating the enantiomers of the formulae (Ia) and/or (Ib) with light in a suitable solvent or solvent mixture in the presence of a base,
wherein the irradiation in step (i) is effected optionally at a temperature of 0° C. to 100° C.

(2) Method according to paragraph (1), wherein Method according to paragraph (1), wherein the irradiation with light in step (i) is effected at a temperature of 30° C. to 70° C.

(3) Method according to paragraph (1) or (2), wherein the irradiation with light in step (i) is effected at a temperature of 40° C. to 60° C.

(4) Method according to any of paragraphs (1) to (3), wherein the solvent or solvent mixture in step (i) is selected from the group consisting of dichloromethane, acetone, toluene, tetrahydrofuran, methanol, 4-methyl-2-pentanone, methyl ethyl ketone, cyclohexanone, acetonitrile, dimethylformamide, dimethylsulfoxide and mixtures thereof.

(5) Method according to any of paragraphs (1) to (4), wherein the solvent or solvent mixture in step (i) is selected from the group consisting of acetone, acetonitrile, dimethylformamide, dimethylsulfoxide and mixtures thereof.

(6) Method according to any of paragraphs (1) to (5), wherein the solvent or solvent mixture in step (i) is selected from the group consisting of acetone, acetonitrile and mixtures thereof.

(7) Method according to any of paragraphs (1) to (6), wherein the concentration range of the enantiomer used in step (i) in the solvent or solvent mixture is 0.05% to 10% (m/v), based on the volume of the solvent or solvent mixture.

(8) Method according to any of paragraphs (1) to (7), wherein the base in step (i) is selected from the group consisting of 1,8-diazabicyclo[5.4.0]undec-7-ene, 1,5-diazabicyclo(4.3.0)non-5-ene, triethylamine, diisopropylethylamine, trimethylamine, tripropylamine, tributylamine, 1,4-diazabicyclo(2.2.2)octane, 4-(dimethylamino)pyridine, TBD, 1,5,7-triazabicyclo[4.4.0]dec-5-ene, 7-methyl-1,5,7-triazabicyclo[4.4.0]dec-5-ene, tetramethylguanidine, N,N,N,N-tetramethyl-1,8-naphthalenediamine, lutidine, pyridine, imidazole, N-methylimidazole, phosphazene and mixtures thereof.

(9) Method according to any of paragraphs (1) to (8), wherein 1 to 20 equivalents of the organic base are used in step (i).

(10) Method according to any of paragraphs (1) to (9), wherein 2 to 15 equivalents of the organic base are used in step (i).

(11) Method according to any of paragraphs (1) to (10), wherein 5 to 12 equivalents of the organic base are used in step (i).

(12) Method according to any of paragraphs (1) to (11), wherein the irradiation in step (i) is effected for a period from 1 hour to 40 hours.

(13) Method according to any of paragraphs (1) to (12), wherein the irradiation in step (i) is effected for a period from 10 hours to 20 hours.

(14) Method for preparing (4S)-4-(4-cyano-2-methoxyphenyl)-5-ethoxy-2,8-dimethyl-1,4-dihydro-1,6-naphthyridine-3-carboxamide of the formula (Ia)

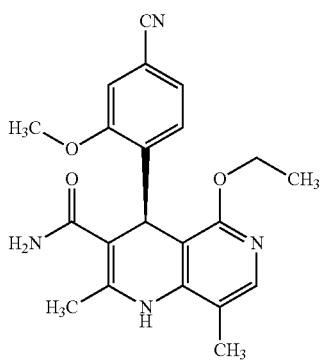

(Ia)

comprising the steps (ii), (iii) and (iv):

(ii) irradiating the compound of the formula (Ib)

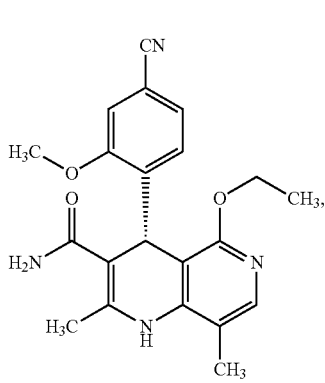

(Ib)

with light in a suitable solvent or solvent mixture in the presence of a base, wherein the compound of the formula (Ib) is converted to a racemic compound of the formula (I)

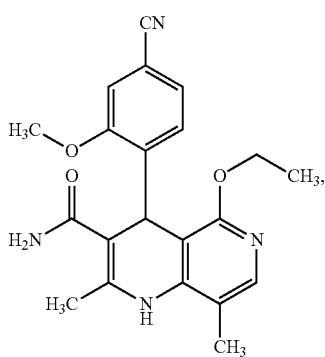

(I)

(iii) optical resolution of this racemic compound (I) from step (ii) using a chiral tartaric acid ester of the formula (III)

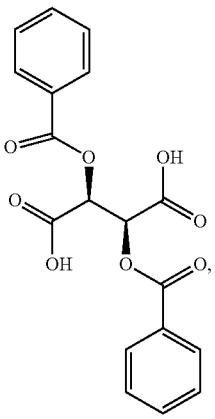

(III)

in a spirits/water mixture, wherein the diastereomeric salt (IVa)

(IVa)

is formed, and (iv) treating the diastereomeric salt (IVa) from step (iii) with a base, wherein the compound of the formula (Ia) is formed.

(15) Method according to paragraph (14), wherein the method further comprises the step (v):

(v) removal of the solvent or the solvent mixture.

(16) Method according to either of paragraphs (14) and (15), wherein the irradiation in step (ii) is effected at a temperature in the range from 0° C. to 100° C.

(17) Method according to any of paragraphs (14) to (16), wherein the irradiation with light in step (ii) is effected at a temperature of 30° C. to 70° C.

(18) Method according to any of paragraphs (14) to (17), wherein the irradiation with light in step (ii) is effected at a temperature of 40° C. to 60° C.

(19) Method according to any of paragraphs (14) to (18), wherein the solvent or solvent mixture in step (ii) is selected from the group consisting of dichloromethane, acetone, toluene, tetrahydrofuran, methanol, 4-methyl-2-pentanone, methyl ethyl ketone, cyclohexanone, acetonitrile, dimethylformamide, dimethylsulfoxide and mixtures thereof.

(20) Method according to any of paragraphs (14) to (19), wherein the solvent or solvent mixture in step (ii) is selected from the group consisting of acetone, acetonitrile, dimethylformamide, dimethylsulfoxide and mixtures thereof.

(21) Method according to any of paragraphs (14) to (20), wherein the solvent or solvent mixture in step (ii) is selected from the group consisting of acetone, acetonitrile and mixtures thereof.

(22) Method according to any of paragraphs (14) to (21), wherein the concentration range of the enantiomer used in step (ii) in the solvent or solvent mixture is 0.05% to 10% (m/v), based on the volume of the solvent or solvent mixture.

(23) Method according to any of paragraphs (14) to (22), wherein the base in step (ii) is selected from the group consisting of 1,8-diazabicyclo[5.4.0]undec-7-ene, 1,5-diazabicyclo(4.3.0)non-5-ene, triethylamine, diisopropylethylamine, trimethylamine, tripropylamine, tributylamine, 1,4-diazabicyclo(2.2.2)octane, 4-(dimethylamino)pyridine, TBD, 1,5,7-triazabicyclo[4.4.0]dec-5-ene, 7-methyl-1,5,7-triazabicyclo[4.4.0]dec-5-ene, tetramethylguanidine, N,N,N,N-tetramethyl-1,8-naphthalenediamine, lutidine, pyridine, imidazole, N-methylimidazole, phosphazene and mixtures thereof.

(24) Method according to any of paragraphs (14) to (23), wherein 1 to 20 equivalents of the organic base are used in step (ii).

(25) Method according to any of paragraphs (14) to (24), wherein 2 to 15 equivalents of the organic base are used in step (ii).

(26) Method according to any of paragraphs (14) to (25), wherein 5 to 12 equivalents of the organic base are used in step (ii).

(27) Method according to any of paragraphs (14) to (26), wherein the irradiation in step (ii) is effected for a period from 1 hours to 40 hours.

(28) Method according to any of paragraphs (14) to (27), wherein the irradiation in step (ii) is effected for a period from 6 hours to 35 hours.

(29) Method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

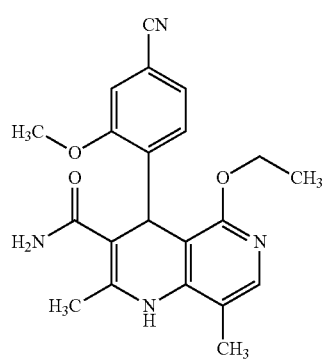

(I)

from the pyridine of the formula (II)

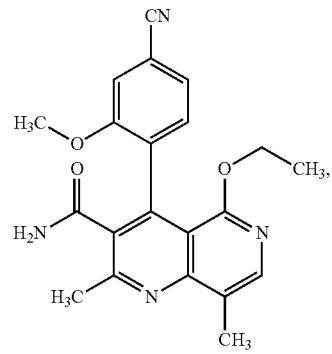

(II)

comprising the step (vi):
(vi) irradiating the compound of the formula (II) with light in a suitable solvent, or solvent mixture, in the presence of a base, wherein the compound according to formula (I) is formed.

(30) Method according to paragraph 29, wherein the irradiation in step (vi) is effected at a temperature of 0° C. to 100° C.

(31) Method according to any of paragraphs (29) to (30), wherein the irradiation with light in step (vi) is effected at a temperature of 30° C. to 70° C.

(32) Method according to any of paragraphs (29) to (31), wherein the irradiation with light in step (vi) is effected at a temperature of 40° C. to 60° C.

(33) Method according to any of paragraphs (29) to (32), wherein the solvent or solvent mixture in step (vi) is selected from the group consisting of dichloromethane, acetone, toluene, tetrahydrofuran, methanol, 4-methyl-2-pentanone, methyl ethyl ketone, cyclohexanone, acetonitrile, dimethylformamide, dimethylsulfoxide and mixtures thereof.

(34) Method according to any of paragraphs (29) to (33), wherein the solvent or solvent mixture in step (vi) is selected from the group consisting of acetone, acetonitrile, dimethylformamide, dimethylsulfoxide and mixtures thereof.

(35) Method according to any of paragraphs (29) to (34), wherein the solvent or solvent mixture in step (vi) is selected from the group consisting of acetone, acetonitrile and mixtures thereof.

(36) Method according to any of paragraphs (29) to (35), wherein the concentration range of the enantiomer used in step (vi) in the solvent or solvent mixture is 0.05% to 10% (m/v), based on the volume of the solvent or solvent mixture.

(37) Method according to any of paragraphs (29) to (36), wherein the base in step (iv) is selected from the group consisting of 1,8-diazabicyclo[5.4.0]undec-7-ene, 1,5-diazabicyclo(4.3.0)non-5-ene, triethylamine, diisopropylethylamine, trimethylamine, tripropylamine, tributylamine, 1,4-diazabicyclo(2.2.2)octane, 4-(dimethylamino)pyridine, TBD, 1,5,7-triazabicyclo[4.4.0]dec-5-ene, 7-methyl-1,5,7-triazabicyclo[4.4.0]dec-5-ene, tetramethylguanidine, N,N,N,N-tetramethyl-1,8-naphthalenediamine, lutidine, pyridine, imidazole, N-methylimidazole, phosphazene and mixtures thereof.

(38) Method according to any of paragraphs (29) to (37), wherein 1 to 20 equivalents of the organic base are used in step (vi).

(39) Method according to any of paragraphs (29) to (38), wherein 2 to 15 equivalents of the organic base are used in step (vi).

(40) Method according to any of paragraphs (29) to (39), wherein 5 to 12 equivalents of the organic base are used in step (vi).

(41) Method according to any of paragraphs (29) to (40), wherein the irradiation in step (vi) is effected for a period from 1 hours to 40 hours.

(42) Method according to any of paragraphs (29) to (41), wherein the irradiation in step (vi) is effected for a period from 10 hours to 20 hours.

EXAMPLES

Experimental

Abbreviations and Acronyms:

| DBU | 1,8-Diazabicyclo[5.4.0]undec-7-ene |
| DBN | 1,5-Diazabicyclo(4.3.0)non-5-ene |
| Hünig's base | Diisopropylethylamine |
| DABCO | 1,4-Diazabicyclo(2.2.2)octane |
| DMAP | 4-(Dimethylamino)pyridine |
| TBD | 1,5,7-Triazabicyclo[4.4.0]dec-5-ene |
| MTBD | 7-Methyl-1,5,7-triazabicyclo[4.4.0]dec-5-ene |
| MEK | Methyl ethyl ketone |
| THF | Tetrahydrofuran |
| DCM | Dichloromethane |
| MIBK | 4-Methyl-2-pentanone |
| EtOH | Ethanol |
| ACN | Acetonitrile |
| DMF | Dimethylformamide |
| DB tartaric acid | Dibenzoyltartaric acid |
| DMSO | Dimethyl sulfoxide |
| o. t. | of theory (in yield) |
| HPLC | High-pressure, high-performance liquid chromatography |
| 1H-NMR | 1H nuclear magnetic resonance spectrometry |
| IT | Internal temperature |
| MS | Mass spectrometry |
| RT | room temperature/retention time |
| RRT | Relative retention time |
| TFA | Trifluoroacetic acid |
| TI | Internal temperature |
| TM | outside temperature |
| XRPD | X-ray powder diffraction |
| spirits | ethanol denatured with 2% toluene |

The table below shows the structures of the compounds recovered in HPLC. The assignment of the retention times in HPLC is shown below.

TABLE

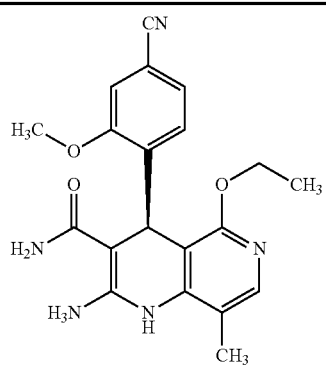

Finerenone (Ia)

TABLE-continued

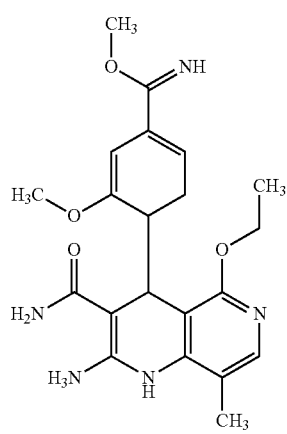

impurity A

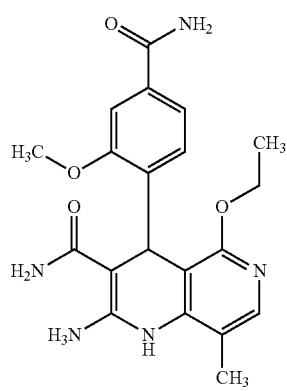

impurity B impurity C (unknown structure, always significantly less than 0.1%)

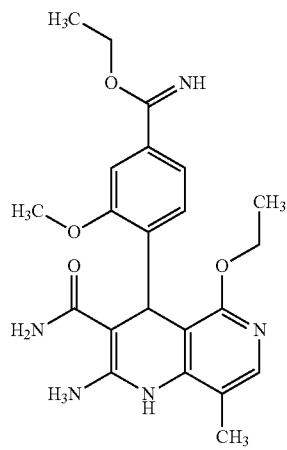

impurity D

TABLE-continued
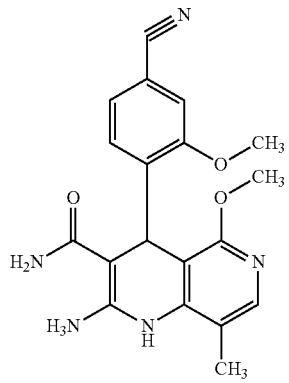
impurity E
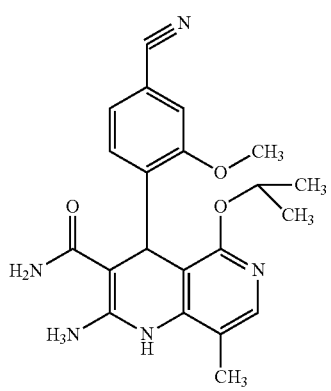
impurity G
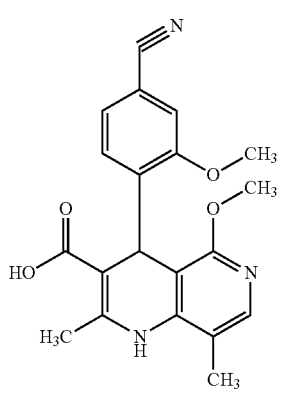
impurity F
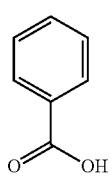
impurity H
TABLE-continued
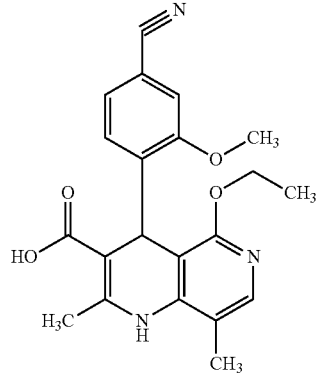 [SMILES: CCOc1ncc(C)c2c1C(c1ccc(C#N)cc1OC)C(C(=O)O)=C(C)N2]
impurity I
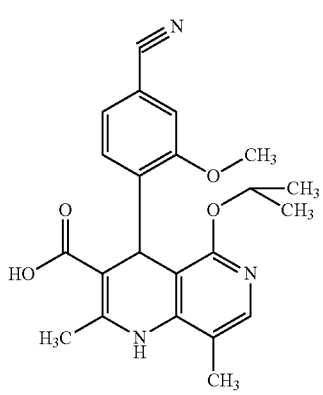 [SMILES: COc1cc(C#N)ccc1C1C(C(=O)O)=C(C)Nc2c(C)cnc(OC(C)C)c21]
impurity J
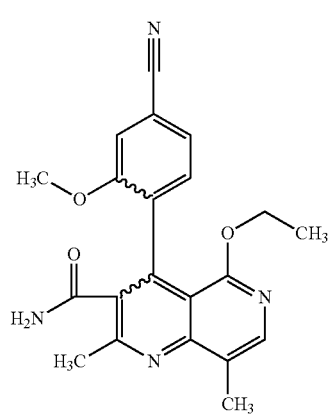 [SMILES: CCOc1ncc(C)c2nc(C)c(C(N)=O)c(-c3ccc(C#N)cc3OC)c12]
impurity K (II)

TABLE-continued

| Content and organic impurities | | RT (min) | RRT |
|---|---|---|---|
| | dibenzoyltartaric acid | about 11.1 | 1.00 |
| 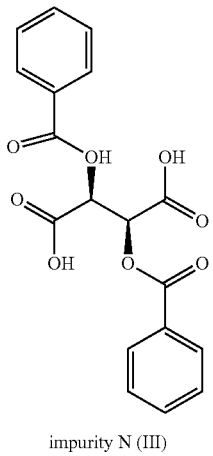 [SMILES: O=C(O[C@H](C(=O)O)[C@H](OC(=O)c1ccccc1)C(=O)O)c1ccccc1] | | | |
| | monobenzoyltartaric acid | about 5.1 | 0.46 |
| | benzoic acid | about 7.6 | 0.69 | impurity N (III)

1) Analytical Method for Checking the Content of Impurities and the Enantiomeric Purity at the Stage of the Dibenzoyltartaric Acid Instrument: ultrahigh-performance liquid chromatograph (having a pressure range of up to 1200 bar with temperature-controlled column oven and UV detector)
Column: YMC Triart C8
  length: 100 mm; internal diameter: 3.0 mm; particle size: 1.9 µm
  Max pressure: 1000 bar
Conditions: 20° C.; 0.50 ml/min; 1.7 µl (10° C.); 240 nm/6 nm
Eluent: A: 0.1% TFA in water; B: acetonitrile

| Gradient | time (min) | A (%) | B (%) |
|---|---|---|---|
| | 0.0 | 90.0 | 10.0 |
| | 15.0 | 35.0 | 65.0 |
| | 16.0 | 20.0 | 80.0 |
| | 20.0 | 20.0 | 80.0 |

Enantiomeric purity:

| | RT (min) | RRT |
|---|---|---|
| (+)-dibenzoyltartaric acid | 2.1 | 1.00 |
| (−)-dibenzoyltartaric acid | 3.9 | 1.86 |

Instrument: high-performance liquid chromatograph with temperature-controlled column oven and UV detector
Column:
Conditions: 40° C.; 2.0 ml/min; 5 µl; 234 nm/6 nm
Eluent: A: heptane; B: 0.1% TFA in ethanol
Isocratic: A (%) 80: B (%) 20

2) Analytical Method for Checking the Content of Impurities and the Enantiomeric Purity at the Stage of the Diastereomeric Salt

| | | RT | RRT |
|---|---|---|---|
| Content and organic impurities | Finerenone (Ia) | 6.2 | 1.00 |
| | impurity A | 3.3 | 0.53 |
| | impurity B | 3.7 | 0.60 |
| | impurity C | 3.9 | 0.62 |
| | impurity D | 4.4 | 0.70 |
| | impurity E | 5.5 | 0.89 |
| | impurity G | 6.8 | 1.10 |
| | impurity F | 7.2 | 1.17 |
| | impurity H | 7.7 | 1.25 |
| | impurity I | 7.8 | 1.27 |
| | impurity J | 8.4 | 1.36 |
| | impurity K | 10.4 | 1.69 |
| | impurity N | 11.1 | 1.80 |

Instrument: ultrahigh-performance liquid chromatograph (having a pressure range of up to 1200 bar with temperature-controlled column oven and UV detector)
Column: YMC Triart C8
  length: 100 mm; internal diameter: 3.0 mm; particle size: 1.9 µm
  Max pressure: 1000 bar
Conditions: 20° C.; 0.50 ml/min; 3.5 µl (10° C.); 242 nm/6 nm
Eluent: A: 0.1% TFA in water; B: acetonitrile

| Gradient: | time (min) | A (%) | B (%) |
|---|---|---|---|
| | 0.0 | 90.0 | 10.0 |
| | 15.0 | 35.0 | 65.0 |
| | 16.0 | 20.0 | 80.0 |
| | 20.0 | 20.0 | 80.0 |

| Enantiomeric purity: | RT (min) | RRT |
|---|---|---|
| Finerenone (Ia) | 5.34 | 1.00 |
| (Ib) | 6.14 | 1.15 |

Instrument: high-performance liquid chromatograph with temperature-controlled column oven and UV detector
Column: Lux 3pm i-Cellulose-5
  length: 150 mm, internal diameter: 4.6 mm, particle size: 3.0 μm
  Max pressure: 300 bar
  Conditions: 40° C.; 1.0 ml/min; 10 μl (20° C.); 252 nm/6 nm
  Eluent: A: 20 mmol ammonium acetate buffer pH 9.0 (1.54 g ammonium acetate in 1 l of Milli-Q water, adjusted to pH 9.0 with ammonia)
  B: acetonitrile
  Isocratic: A (%) 50: B (%) 50

3) Analytical Method for Checking the Content of Impurities and the Enantiomeric Purity at the Stage of Crude Finerenone (Ia).

| Content and organic impurities | RT (min) | RRT |
|---|---|---|
| Finerenone (Ia) | 6.2 | 1.00 |
| impurity A | 3.3 | 0.53 |
| impurity B | 3.7 | 0.60 |
| impurity C | 3.9 | 0.62 |
| impurity D | 4.4 | 0.70 |
| impurity E | 5.5 | 0.89 |
| impurity F | 5.6 | 0.91 |
| impurity G | 6.8 | 1.10 |
| impurity H | 7.6 | 1.23 |
| impurity K | 10.4 | 1.68 |
| impurity N | 11.1 | 1.79 |

Instrument: ultrahigh-performance liquid chromatograph (having a pressure range of up to 1200 bar with temperature-controlled column oven and UV detector)
Column: YMC Triart C8
  length: 100 mm; internal diameter: 3.0 mm; particle size: 1.9 μm
  Max pressure: 1000 bar
  Conditions: 20° C.; 0.50 ml/min; 1.7 μl (10° C.); 252 nm/6 nm and 230 nm/6 nm for the evaluation of DB-tartaric acid
  Eluent: A: 0.1% TFA in water; B: acetonitrile

| Gradient: | time (min) | A | B (%) |
|---|---|---|---|
| | 0.0 | 90. | 10.0 |
| | 15.0 | 35. | 65.0 |
| | 16.0 | 20. | 80.0 |
| | 20.0 | 20. | 80.0 |

| Enantiomeric purity: | RT (min) | RRT |
|---|---|---|
| Finerenone (Ia) | about | 1.00 |
| Method A (Ib) | about 9 | 0.82 |

Instrument: high-performance liquid chromatograph with temperature-controlled column oven and UV detector
Column: Chiralpak IA
  length: 250 mm, internal diameter: 4.6 mm, particle size: 5.0 μm
  Max pressure: 300 bar
  Conditions: 40° C.; 0.8 ml/min; 5 μl (20° C.); 255 nm/6 nm
  Eluent: A: acetonitrile; B: methyl tert-butyl ether (MTBE)
  Isocratic: A (%) 90: B (%) 10
  Enantiomeric purity

| Method B | RT(min) | RRT |
|---|---|---|
| Finerenone (Ia) | 5.7 | 1.00 |
| Enantiomer (Ib) | 6.8 | 1.19 |

Instrument/detector: high-performance liquid chromatograph with temperature-controlled column oven, UV detector
and data evaluation system
Measurement wavelength: 252 nm
Oven temperature: 40° C.
Column: Chiralpak IC
length: 150 mm, internal diameter: 4.6 mm, particle size: 3 μm
Mobile phase:
A: 50% buffer 20 mM NH4OAc acetate pH 9
B: 50% acetonitrile
Flow rate: 1 ml/min.
Elution time: 8 min.
Equilibration: unnecessary, isocratic
Sample solvent: eluent
Sample solution: about 0.5 mg/ml of the substance racemate, dissolved in sample solvent
Comparative solution: A comparative solution analogous to the sample solution is prepared
Injection volume: 10 μl The measured values stated in the examples below for enantiomer determination were all determined by Method B. Some values, especially those of the batches prepared in the pilot plant, were reanalysed with Method A for comparison, and gave comparable results.

The HPLC analysis data given in the examples which follow with respect to purity and content of the end product pure finerenone (Ia) relate solely to impurities present in the product in an amount of >0.05%. This is essentially impurity E. All other impurities shown in the table listed above are generally <0.05%. The structure of such impurities was determined by isolation from enriched mother liquors.

The following instruments were used in the examples:
Oxygen Measuring Device

An oxygen measuring device from "pyro science sensor technology" was used. It was the "Firesting 02" model, which measures and saves oxygen contents using a fibre-optic fibre and optional logging.

Reaction Apparatuses

For screening tests (up to 1000 ml reaction volumes), initially a small, self-built system with reactors and accessories from Peschl Ultraviolett was used. Likewise, initial approaches on a larger scale (between 1000 and 2500 ml reaction volumes) were carried out in a self-built system with parts from different manufacturers, also from Peschl Ultraviolett among others. Subsequently, screening and large batches were carried out in compact reaction plants from Peschl Ultraviolett.

To implement the individual batches, either batch or sideloop reactors and also falling film reactors were used.

Uv Lamps

For the individual batches, low pressure mercury and LED lamps from Peschl Ultraviolett were used. In detail, these were TQ 150 (150 W power), TQ 1000 (1000 W) and TQ 2000 (2000 W) and LED lamps (40 W power) with wavelengths of 365 nm and 405 nm. The low pressure mercury lamps (TQ XXX HG) produced light in the spectral range of 260 to 600 nm.

"Filters" and Glass Holders for the Lamps

The respective UV lamps were mounted in glass holders which consisted of clear quartz or Duran glass. The Duran glass filters below 310 nm.

Synthetic Air

Synthetic air of 20% oxygen/80% nitrogen and also 30% oxygen/70% nitrogen was used.

In the case of even lower oxygen contents, the synthetic air was diluted with nitrogen.

The wrong enantiomer (Ib), which is used in the photochemical recycling process, may be obtained on the one hand by optical resolution via SMB separation on a chiral stationary phase (using an acetonitrile/methanol eluent mixture, for example 70:30 and for example Phase Chiralpak AS-V, 20 μm), see WO 2016/016287 A1, on the other hand may be prepared by optical resolution using (+)-O,O-dibenzoyl-D-tartaric acid.

Since the antipodes (La) and (Ib) do not differ in their photochemical properties, both compounds were used in some instances since the results are transferable. Therefore, photochemical recycling was developed using both antipodes, with the aim however to racemise on a large scale the corresponding wrong enantiomer (Ib).

Example 1

Laboratory Batch Using Anhydrous (+)-O,O-Dibenzoyl-D-Tartaric Acid (III)

Example 1a

Tartrate salt (IVa) preparation of (4S)-4-(4-cyano-2-methoxyphenyl)-5-ethoxy-2,8-dimethyl-1,4-dihydro-1,6-naphthyridine-3-carboxamide (Ia)

250 g (660.616 mmol) of racemate (I) (rac (4S,4R)-4-(4-cyano-2-methoxyphenyl)-5-ethoxy-2,8-dimethyl-1,4-dihydro-1,6-naphthyridine-3-carboxamide) were initially charged in 3500 ml of a mixture consisting of ethanol, denatured with toluene/water=75:25 (v/v) at room temperature (ca. 23° C.). 130.2 g (363.339 mmol) of (+)-O,O-dibenzoyl-D-tartaric acid (III) were added using a funnel for solids, subsequently rinsing with 250 ml of a mixture consisting of ethanol (denatured with toluene)/water=75:25 (v/v). The resulting suspension was heated to an internal temperature of 75° C. over 0.75 hours and then stirred at this temperature for 3.0 hours. Subsequently, using a cooling ramp, the mixture was cooled to 23° C. over 5.0 hours and then stirred at this temperature overnight (about 16 hours). The suspension was filtered off through a frit, rinsing once with 250 ml of a mixture consisting of ethanol (denatured with toluene)/water=75:25 (v/v). Wet yield: 334.7 g. The wet product was then dried overnight (about 16 hours) at 50° C. under reduced pressure (<100 mbar). Yield: 250.2 g (100.08% of theory) of a colourless crystalline powder.

Analytical Results:

| | |
|---|---|
| Finerenone (Ia) | 47.2% by weight (HPLC) |
| Enantiomeric excess | 97.68% e.e. |
| Largest unknown secondary component at Rt 5.606 min. | 0.47% |
| Residual solvents: | |
| EtOH | 2.24% |
| toluene | 0.0% |

MS (Method IC): m/z=379 [M]$^+$;

$^1$H-NMR (400 MHz, DMSO-d$_6$): δ=1.05 (t, 3H), 2.12 (s, 3H), 2.18 (s, 3H), 3.82 (s, 3H), 3.99-4.07 (m, 2H), 5.39 (s, 1H), 5,89 (s, 2H), 6.60-6.84 (m (broad signal), 2H), 7.14 (d, 1H), 7.28 (dd, 1H), 7.37 (d, 1H), 7.55 (s, 1H), 7,61 (t, 4H), 7.69 (s, 1H), 7,75 (t, 2H), 8,04 (d, 4H), 12,50-15,40 (very broad signal, 2H) and signal from DMSO solvent and elevated water signal: δ=2.5-2.6, and small peaks at δ=3.40-3.50 (q) and δ=1.05-1.10 (t), superimposed signal from residual ethanol solvent.

Example 1b

Preparation of crude product (Ia) of (4S)-4-(4-cyano-2-methoxyphenyl)-5-ethoxy-2,8-dimethyl-1,4-dihydro-1,6-naphthyridine-3-carboxamide At room temperature, 248 g of the compound (IVa) prepared in Example 1a were suspended in 2480 ml of a mixture consisting of ethanol (denatured with toluene)/water=20:80 (v/v) (the pH was determined to be pH=4). Subsequently, 819.6 g of an aqueous sodium phosphate solution (100 g of sodium phosphate dissolved in 1000 ml of water) were added dropwise over 60 minutes and the pH was adjusted to pH=7.2. The mixture was stirred at 23° C. for a further 50 minutes (pH=7.1).

Subsequently, 98.3 g of an aqueous sodium phosphate solution (100 g of sodium phosphate dissolved in 1000 ml of water) were added dropwise over 10 minutes and the pH was adjusted to pH==7.5. Over one hour, the mixture was heated to an internal temperature of 50° C. and stirred at this temperature for 3.0 hours. The mixture was cooled to 22° C. over one hour and stirred at this temperature for another hour. The crystals are filtered off through a frit and washed once with 200 ml and once with 100 ml of a mixture consisting of ethanol (denatured with toluene)/water=20:80 (v/v) and twice with 200 g of water. Wet yield: 263.4 g. The wet product was then dried over the weekend (>48 hours) at 50° C. under reduced pressure (<100 mbar). Yield: 116.9 g (93.52% of theory) of a colourless crystalline powder.

Analytical Results:

| | |
|---|---|
| Finerenone (Ia) | Purity: 99.86 area % (HPLC); Content: 100.0% by weight |
| Enantiomeric excess | 97.02% e.e. |
| Largest secondary component impurity E | 0.07% |
| Residual solvents: | |
| EtOH | 0.19% |
| toluene | 0.13% |
| water (Karl Fischer) | 0.042% |

MS (Method IC): m/z=379 [M]$^+$;

$^1$H-NMR (400 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m (broad signal), 2H), 7.14 (d, 1H), 7.28 (dd, 1H), 7.37 (d, 1H), 7.55 (s, 1H), 7.69 (s, 1H) and signal from DMSO solvent and significantly enhanced water signal: δ=2.5-2.6, and a very small peak at δ=3.38 (not assignable).

Example 1c

Preparation of pure product (Ia) of (4S)-4-(4-cyano-2-methoxyphenyl)-5-ethoxy-2,8-dimethyl-1,4-dihydro-1,6-naphthyridine-3-carboxamide 116.0 g of the crude product (Ia) prepared in Example 1b were suspended in 2330 ml of ethanol (denatured with toluene) and then heated to reflux. On heating, the product went into solution. Stirring was continued at this temperature for one hour. The solution was filtered off through a heated pressure filter (T=75° C.) and the pressure filter was then rinsed with 30 ml of ethanol (denatured with toluene). The solvent was then distilled off (about 1920 ml was distilled off) until a final volume of about 4-fold (based on the substance used: 116 g×4~484 ml) had been attained. The mixture was then cooled to internal temperature 23° C. (over about 1.5 to 2 hours). The mixture was then stirred at internal temperature 3° C. for 2 hours. The product was filtered off and rinsed once with 100 ml of ethanol (denatured with toluene). Wet yield: 124 g. The wet product was dried at 50° C. over the weekend (>48 h) under reduced pressure (<100 mbar). Yield: 112.6 g (97.07% of theory) of a colourless crystalline powder (fine needle-like crystals).
Analytical Results:

| Finerenone (Ia) | Purity: 99.86 area (HPLC); Content: 99.5% by weight |
|---|---|
| Enantiomeric excess | 100% e.e. |
| Largest secondary component impurity E | 0.07% |
| Residual solvents: | |
| EtOH | 0.05% |
| toluene | 0.00% |
| water (Karl Fischer) | 0.00% |

MS (Method IC): m/z=379 [M]$^+$;
$^1$H-NMR (400 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m (broad signal), 2H), 7.14 (d, 1H), 7.28 (dd, 1H), 7.37 (d, 1H), 7.55 (s, 1H), 7.69 (s, 1H) and small signals from DMSO solvent and water at δ=2.5-2.6 and a very small peak at δ=3.38 (not assignable)
Modification: Mod A (as defined in WO2016/016287 A1)

Example 1d

Isolation of the wrong enantiomer (Ib) from the mother liquor of (4R)-4-(4-cyano-2-methoxyphenyl)-5-ethoxy-2,8-dimethyl-1,4-dihydro-1,6-naphthyridine-3-carboxamide At room temperature, combined mother liquor and wash solution from Example 1a (about 3750 ml of a yellowish solution, pH=4.5) were adjusted to pH=7.5 by addition of 101.1 g of an aqueous sodium phosphate solution (100 g dissolved in 1 l of water). Under reduced pressure (85 to 65 mbar, internal temperature 38° to 20° C.), the spirits were then substantially distilled off and the mixture was reduced to an end volume of about 0.85 l. The mixture was cooled to room temperature and the precipitated suspension was stirred over the weekend (>48 hours) and then at 22° C. for a further 2 hours. The suspension was filtered off with suction and washed twice with in each case 200 ml of water. Wet yield: 139.1 g. The wet product was dried at 50° C. overnight (about 16 h) under reduced pressure (<100 mbar). Yield: 103.1 g (82.48% of theory based on the racemate (I) used in Example 1a).

| Finerenone enantiomer (Ib) | Purity: 99.75 area % (HPLC); Content: 99.2% by weight |
|---|---|
| Enantiomeric excess | 99.34% e.e. |
| Largest secondary component impurity E | 0.12% |
| (+)-O,O-Dibenzoyl-D-tartaric acid | 0.14%/31%/0.05% by weight % |
| Water | 0.102% |

Example 2

Start-Up Experiments on Photochemistry

Influence of solvent (screening experiments to select the optimal solvent)

S-Finerenone (4S)-4-(4-cyano-2-methoxyphenyl)-5-ethoxy-2,8-dimethyl-1,4-dihydro-1,6-naphthyridine-3-carboxamide (>99% e.e.) was irradiated in a solvent or solvent mixture (see Tables) with an LED at 365 nm for 10 minutes. 2 equivalents of DBU were used. The concentration was ca. 1.5%. The following tables show the results:

At the start, surprisingly large amounts of pyridine compound (II) were found:

| Solvent | (II) % | (I) % |
|---|---|---|
| Acetone | 59.7 | 39.60 |
| DMF | 68.8 | 27.5 |
| NMP | 74.1 | 19.3 |
| DCM | 84.4 | 15.6 |
| Cyclohexanone | 76 | 16 |
| MEK | 64.9 | 34.1 |
| Acetone | 59.7 | 39.60 |
| DMF | 68.8 | 27.5 |
| DMF/Acetone 80:20 | 74.3 | 19.9 |
| DMF/Acetone 50:50 | 69.4 | 28.1 |
| MEK | 64.9 | 34.1 |
| MEK/Acetone 80:20 | 73.2 | 25.5 |
| MEK/Acetone 50:50 | 71.6 | 26.9 |
| DCM | 84.4 | 15.6 |
| DCM/Acetone 50:50 | 78.5 | 19.9 |

Example 3

Start-Up Experiments on Photochemistry

Influence of base (screening experiments to select the optimal base)

S-Finerenone (4S)-4-(4-cyano-2-methoxyphenyl)-5-ethoxy-2,8-dimethyl-1,4-dihydro-1,6-naphthyridine-3-carboxamide (>99% e.e.) was irradiated in acetone with an LED at 365 nm for 10 minutes. 2 equivalents of base were used. The concentration was ca. 1.5%. The following tables show the results:

| Base | (II) % | (I) % |
|---|---|---|
| DBN | 50.5 | 49.5 |
| TBD | 74.4 | 25.7 |
| DBU | 59.7 | 39.6 |

Example 4

Solvent: Acetonitrile

Example 4a

Irradiation of finerenone (Ia) (4S)-4-(4-cyano-2-methoxyphenyl)-5-ethoxy-2,8-dimethyl-1,4-dihydro-1,6-naphthyridine-3-carboxamide for the preparation of rac (4S, 4R)-4-(4-cyano-2-methoxyphenyl)-5-ethoxy-2,8-dimethyl-1,4-dihydro-1,6-naphthyridine-3-carboxamide (I)

Equipment: Photo loop reactor FT03, UV lamp Q1023, Watson-Marlow 620s peristaltic pump (with integrated GORE STA-PURE pump tubing) at 70 rpm, 2 thermostats at 50° C. for reactor and receiver, $N_2$ through receiver and lamp.

21.16 g of S-finerenone (4S)-4-(4-cyano-2-methoxyphenyl)-5-ethoxy-2,8-dimethyl-1,4-dihydro-1,6-naphthyridine-3-carboxamide >99% e.e.) were dissolved in 2.5 L of acetonitrile (1949.99 g) and DBU 51.30 g (6 equivalents) were added. The reaction was started by switching on the lamp, initially gassed for 30 minutes with synthetic air (30% oxygen), and subsequently left under a constant nitrogen stream. After 5 hours, synthetic air (30% 02) was introduced for a further hour and then again adjusted to a constant nitrogen stream. Total irradiation time: 16 h. After the reaction was complete, a sample measurement of the reaction solution was measured: 12% e.e., purity: 87%, content: 81%.

The reaction solution was then worked-up.

The reaction solution was concentrated to 150 mL. 500 mL of water were then added dropwise with stirring over 3 h. After 200 mL had been dripped in, a milky precipitate was observed. After 300 mL, the solution became cloudy. The mixture was stirred at room temperature (ca. 20° C.) for 24 hours. The suspension was filtered and the product was washed with 100 mL of water. The product was dried over 72 hours at 45° C. and 60 mbar.

Yield: 16.02 g (76% of theory) of a colourless crystalline powder (I rac (4S,4R)-4-(4-cyano-2-methoxyphenyl)-5-ethoxy-2,8-dimethyl-1,4-dihydro-1,6-naphthyridine-3-carboxamide)

Analysis:
Solid substance content: 97.3%
Enantiomeric excess: 0.9%
Purity: 98.30 area % (HPLC)

Example 4b

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (I)

In an analogous manner, as described in Example 4a, the wrong enantiomer was irradiated and evaluated after the reaction was complete.

Equipment: Photo loop reactor, UV lamp TQ 150 (stage 1), Duran glass tube, circulating pump, thermostat (50° C.), 5 mm layer thickness.

2.13 g of the wrong enantiomer (Ib) (4R)-4-(4-cyano-2-methoxyphenyl)-5-ethoxy-2,8-dimethyl-1,4-dihydro-1,6-naphthyridine-3-carboxamide were dissolved in 250 mL of acetonitrile (196.69 g) and 4.95 g of DBU (6 equivalents) were added. The reaction was started by switching on the lamp and the solution was flooded with synthetic air for 30 minutes. The reaction was then left under a constant nitrogen stream. Total irradiation time: 8.5 h. After the reaction was complete, a sample measurement of the reaction solution was measured: 9% e.e., purity: 91%, content: 91%

Example 4c

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (I)

In an analogous manner, as described in Example 4a, the wrong enantiomer was irradiated and evaluated after the reaction was complete.

Equipment: Photo loop reactor, UV lamp TQ 150 (stage 1), Duran glass tube, circulating pump, thermostat (50° C.), 5 mm layer thickness. 2.11 g of the wrong enantiomer (Ib) (4R)-4-(4-cyano-2-methoxyphenyl)-5-ethoxy-2,8-dimethyl-1,4-dihydro-1,6-naphthyridine-3-carboxamide were dissolved in 250 mL of acetonitrile (195 g) and 2.55 g of DBU (3 equivalents) were added. The reaction was started by switching on the lamp and the solution was flooded with synthetic air for 30 minutes. The reaction was then left under a constant nitrogen stream. Total irradiation time: 13 h.

After the reaction was complete, a sample measurement of the reaction solution was measured: 10.7% e.e. purity: 95.93%, content: 97%.

Example 4d

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (I)

In an analogous manner, as described in Example 4a, the wrong enantiomer was irradiated and evaluated after the reaction was complete.

Equipment: Photo loop reactor, UV lamp TQ 150 (stage 1), Duran glass tube, circulating pump, thermostat (50° C.), 5 mm layer thickness.

2.15 g of the wrong enantiomer (Ib) (4R)-4-(4-cyano-2-methoxyphenyl)-5-ethoxy-2,8-dimethyl-1,4-dihydro-1,6-naphthyridine-3-carboxamide were dissolved in 250 mL of acetonitrile (195 g) and 5.13 g of DBU (6 equivalents) were added. The reaction was started by switching on the lamp and the solution was flooded with synthetic air for 30 minutes. The reaction was then left under a constant nitrogen stream. Total irradiation time: 7 h 45 min.

After the reaction was complete, a sample measurement of the reaction solution was measured: 15% e.e. purity: 95.4%, content: 97%.

Example 4e

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (1)

In an analogous manner, as described in Example 4a, the wrong enantiomer was irradiated and evaluated after the reaction was complete.

Equipment: Photo loop reactor, UV lamp TQ 150 (stage 1), Duran glass tube, circulating pump, thermostat (50° C.), 5 mm layer thickness.

2.12 g of the wrong enantiomer (Ib) (4R)-4-(4-cyano-2-methoxyphenyl)-5-ethoxy-2,8-dimethyl-1,4-dihydro-1,6-naphthyridine-3-carboxamide were dissolved in 250 mL of acetonitrile (195 g) and 5.12 g of DBU (6 equivalents) were added. The reaction was started by switching on the lamp and the solution was flooded with synthetic air for 15 minutes. The reaction was then left under a constant nitrogen stream. Total irradiation time: 8 h 7 min.

After the reaction was complete, a sample measurement of the reaction solution was measured: 12.6% e.e. purity: 95.4%, content: 97.4%.

Example 4f

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (I)

In an analogous manner, as described in Example 4a, the wrong enantiomer was irradiated and evaluated after the reaction was complete.

Equipment: Photo loop reactor FT03, slit width 1.0 mm, UV lamp Q1023, Ismatec MCP-Z gear pump, 2.4 L/m flow rate, 2 thermostats at 50° C. for reactor and receiver, nitrogen through receiver and lamp. Nitrogen stream receiver: ca. 360 mL/min, regulation of synthetic air to adjust a defined oxygen content of 0.5% 10.62 g of the wrong enantiomer (Ib) (4R)-4-(4-cyano-2-methoxyphenyl)-5-ethoxy-2,8-dimethyl-1,4-dihydro-1,6-naphthyridine-3-carboxamide were dissolved in 2.5 L of acetonitrile (1946.32 g) and 25.23 g of DBU (6 equivalents) were added. The reaction mixture was gassed constantly with a stream of nitrogen and oxygen, the oxygen content here being regulated to 0.5%. The reaction was started by switching on the lamp. After 6 hours, the irradiation was stopped and the solution was stored at RT overnight under nitrogen/oxygen. Continuation: After 8 hours, the irradiation was stopped and the solution was stored at RT overnight under nitrogen/oxygen. Continuation: After 2 hours, oxygen regulation switched off. Stopped after 5 hours and the batch completed. Total irradiation time: 19.5 h.

After the reaction was complete, a sample measurement of the reaction solution was measured: 8.22% e.e., purity: 91.47%.

Example 4 g

Irradiation of the wrong enantiomer (Ib) (4R)-4-(4-cyano-2-methoxyphenyl)-5-ethoxy-2,8-dimethyl-1,4-dihydro-1,6-naphthvridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (I)

In an analogous manner, as described in Example 4a, the wrong enantiomer was irradiated and evaluated after the reaction was complete.

Equipment: Photo loop reactor FT03, slit width 1.0 mm, UV lamp Q1023, Watson-Marlow peristaltic pump, 4 L/min flow rate, 2 thermostats at 45° C. for reactor and receiver, nitrogen through receiver and lamp. Nitrogen stream receiver: ca. 500 mL/min, regulation of synthetic air to adjust a defined oxygen content of 18.0%.

7.52 g of the wrong enantiomer (Ib) (4R)-4-(4-cyano-2-methoxyphenyl)-5-ethoxy-2,8-dimethyl-1,4-dihydro-1,6-naphthyridine-3-carboxamide were dissolved in 2.5 L of acetonitrile (1952.7 g) and 18.1 g of DBU (6 equivalents) were added. The reaction mixture was initially gassed constantly with a stream of synthetic air for 30 minutes, the oxygen content here being regulated to 18.6%.

After 30 minutes, this was switched to pure nitrogen and the oxygen content fell to 0% within about 75 minutes. The reaction was started by switching on the lamp. After 8.5 hours, the irradiation was stopped. Total irradiation time: 8.5 h.

After the reaction was complete, a sample measurement of the reaction solution was measured: 8.41% e.e., purity: 89.66%.

Example 4 h

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (I)

In an analogous manner, as described in Example 4a, the wrong enantiomer was irradiated and evaluated after the reaction was complete.

Equipment: Photo loop reactor FT03, slit width 1.0 mm, UV lamp Q1023, Watson-Marlow peristaltic pump, 4 L/min flow rate, 2 thermostats at 45° C. for reactor and receiver, nitrogen through receiver and lamp. Nitrogen stream receiver: ca. 500 mL/min, regulation of synthetic air to adjust to a defined oxygen content of 17.0%. Start up to 30 minutes: oxygen content 16.7%. 30 minutes to 8 hours: oxygen content 0%.

7.50 g of the wrong enantiomer (Ib) (4R)-4-(4-cyano-2-methoxyphenyl)-5-ethoxy-2,8-dimethyl-1,4-dihydro-1,6-naphthyridine-3-carboxamide were dissolved in 2.5 L of acetonitrile (1951 g) and 17.4 g of DBU (6 equivalents) were added. The reaction mixture was initially gassed constantly with a stream of synthetic air for 30 minutes, the oxygen content here being regulated to 16.7%. After 30 minutes, this was switched to pure nitrogen and the oxygen content fell to 0% within about 40 minutes. The reaction was started by switching on the lamp. After 8 hours, the irradiation was stopped. Total irradiation time: 8 h.

After the reaction was complete, a sample measurement of the reaction solution was measured: 4.08% e.e. Purity: 87.55%.

Example 4i

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (I)

In an analogous manner, as described in Example 4a, the wrong enantiomer was irradiated and evaluated after the reaction was complete.

Equipment: Photo falling film reactor FORA01, UV lamp TLED 100/365 nm, thermostat at 45° C. for reactor and receiver, nitrogen and oxygen through receiver and reactor. Nitrogen stream receiver: ca. 300 mL/min, regulation of synthetic air to adjust to a defined oxygen content of 18.0% or 0%.

3.41 g of the wrong enantiomer (Ib) (4R)-4-(4-cyano-2-methoxyphenyl)-5-ethoxy-2,8-dimethyl-1,4-dihydro-1,6-naphthyridine-3-carboxamide were dissolved in 450 mL of ACN (350 g) and 8.2 g of DBU (6 equivalents) were added. The reaction mixture was initially gassed constantly with a stream of synthetic air for 30 minutes, the oxygen content here being regulated to 18.4%. After 30 minutes, this was switched to pure nitrogen and the oxygen content fell to 0.4% within about 30 minutes. After 60 minutes, the oxygen content was 0.0%. The irradiation was stopped after 8 h, the reaction mixture was stored overnight at 20° C. under nitrogen in the receiver vessel. Total irradiation time: 8 h.

After the reaction was complete, a sample measurement of the reaction solution was measured: 9.45% e.e., purity: 83.02%.

Example 5

Solvent: DMF Dimethylformamide

Example 5a

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (I)

In an analogous manner, as described in Example 4a, the wrong enantiomer (Ib) was irradiated and evaluated after the reaction was complete.

Equipment: EVO photoreactor FoRA02 with falling film reactor and TLED365 lamp for 8 hours and TQ2000 lamp for 2 hours, in each case quartz shell tube 35.0 g of (4R)-4-(4-cyano-2-methoxyphenyl)-5-ethoxy-2,8-dimethyl-1,4-dihydro-1,6-naphthyridine-3-carboxamide (Ib) and (4S)-4-(4-cyano-2-methoxyphenyl)-5-ethoxy-2,8-dimethyl-1,4-dihydro-1,6-naphthyridine-3-carboxamide were dissolved in 2500 mL of DMF (2350 g) and 84.5 g of DBU (6 equivalents) were added. The reaction mixture was transferred to a reactor and the thermostat set to 45° C. Synthetic air was fed in, the oxygen content in the reactor was then 18.2%. The circulating pump was switched on and the flow control regulated to ca. 90 g/min. The temperature of the receiver was adjusted to 45° C. and the temperature of the reactor was set to 44° C. Sampling was started in order to determine the oxygen content.

At t=0 min with lamp ignition at 100% power, the oxygen content was 18%.

At t=30 min switch to nitrogen injection.

At t=120 min an oxygen sample is measured, result: Oxygen=0.0%

At t=240 min an oxygen sample is measured, result: Oxygen=0.0%

At t=420 min an oxygen sample is measured, result: Oxygen=0.0%

The lamp and the thermostat, and also the pump, were then switched off. The nitrogen supply ran overnight. Then, the TQ2000 lamp was reset for carrying out further irradiation.

After restart, an oxygen sample was again measured, oxygen result=0.0%.

Then the lamp and the pump were switched off and the experiment was terminated.

After the reaction was complete, a sample measurement of the reaction solution was measured: 3.45% e.e., purity: 94.54%

Example 5b

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (II)

In an analogous manner, as described in Example 4a, the wrong enantiomer was irradiated and evaluated after the reaction was complete.

The reaction kinetics were investigated.

Equipment: Large photo loop reactor, UV lamp Q1023, 100% power (U=150V, I=6.8), quartz shell tube, Duran dip finger, 2 thermostats @50° C., Watson-Marlow 620s peristaltic pump (with GORE STA-PURE Pump Tubing incorporated) at 70 rpm, reactor inner wall and checked and cleaned before batch. Nitrogen passed through lamp and receiver.

40.54 g of (4R)-4-(4-cyano-2-methoxyphenyl)-5-ethoxy-2,8-dimethyl-1,4-dihydro-1,6-naphthyridine-3-carboxamide (Ib) were added to 2.0 L (1881.52 g) of DMF and then 95.84 mL (6 equivalents, 95.91 g) of DBU were added thereto and the mixture was then degassed in an ultrasound bath for 10 minutes. This reaction mixture was then transferred (under nitrogen) to a storage vessel and rinsed with 0.7 L of DMF (696.95 g). The reaction mixture was then equilibrated for 15 minutes under nitrogen at a flow rate of 120 L/h. The reaction was started by switching on the UV lamp. The reaction solution was discharged over the weekend and rinsed with 400 mL of DMF (372.19 g). The reaction was continued thereafter. Total irradiation time: 34 h. The following table shows the result of the racemization over 34 hours:

| Sampling | % e.e. |
|---|---|
| Starting sample 0 h | 100.0 |
| 1 h | 98.7 |
| 2 h | 95.8 |
| 3 h | 91.6 |
| 4 h | 86.3 |
| 5 h | 82.3 |
| 6 h | 76.9 |
| 7 h | 67.2 |
| 9 h | 49.2 |
| 11 h | 38.9 |
| 12.5 h | 35.1 |

-continued

| Sampling | % e.e. |
|---|---|
| 14.5 h | 30.8 |
| 16 h | 27.7 |
| 18 h | 24.8 |
| 20 h | 22.1 |
| 22 h | 19.8 |
| 24 h | 18.5 |
| 26 h | 17.2 |
| 29 h | 15.2 |
| 32 h | 13.4 |
| End 34 h | 12.3 |

Example 6

Solvent mixture: Acetonitrile/Acetone=19:1

Irradiation of the wrong enantiomer (4R)-4-(4-cyano-2-methoxyphenyl)-5-ethoxy-2,8-dimethyl-1,4-dihydro-1,6-naphthyridine-3-carboxamide (Ib) for the preparation of rac (4S,4R)-4-(4-cyano-2-methoxyphenyl)-5-ethoxy-2,8-dimethyl-1,4-dihydro-1,6-naphthyridine-3-carboxamide (1)

In an analogous manner, as described in Example 4a, the wrong enantiomer was irradiated and evaluated after the reaction was complete.
Equipment: Photo loop reactor, UV lamp TQ 150 (stage 1), Duran, circulating pump, thermostat (50° C.), 5 mm layer thickness.

2.12 g of (4R)-4-(4-cyano-2-methoxyphenyl)-5-ethoxy-2,8-dimethyl-1,4-dihydro-1,6-naphthyridine-3-carboxamide (Ib) were dissolved in 237.5 mL (190.08 g) of acetonitrile and 12.5 mL (9.48 g) of acetone and 4.89 g of DBU (6 equivalents) were added. The reaction was started by switching on the lamp and at the start left under a constant stream of nitrogen. After a reaction time of 6 h 40 min, the collecting vessel was aerated for 10 min. After 7 h 15 min up to 8 h and from 9 h 30 min to 13 h 10 min reaction time, the nitrogen stream was discontinued. Between and after these phases, the reaction was carried out under a constant nitrogen stream. The total irradiation time was 16 h 10 min.

After the reaction was complete, a sample measurement of the reaction solution was measured: 9% ee, purity: 90%, content: 90%

Example 7

Solvent: acetone

Irradiation of the wrong enantiomer (Ib) (4R)-4-(4-cyano-2-methoxyphenyl)-5-ethoxy-2,8-dimethyl-1,4-dihydro-1,6-naphthyridine-3-carboxamide for the preparation of rac (4S,4R)-4-(4-cyano-2-methoxyphenyl)-5-ethoxy-2,8-dimethyl-1,4-dihydro-1,6-naphthyridine-3-carboxamide (I)

In an analogous manner, as described in Example 4a, the wrong enantiomer was irradiated and evaluated after the reaction was complete.
Equipment:
Large photo loop reactor, UV lamp Q1023, 100% power (U=150V, 1=6.8), quartz shell tube, Duran dip finger, 2 thermostats @50° C., Watson-Marlow 620s peristaltic pump (with GORE STA-PURE Pump Tubing incorporated) at 70 rpm, reactor inner wall checked and cleaned before batch. Nitrogen passed through reactor and receiver.

20.50 g of wrong enantiomer (4R)-4-(4-cyano-2-methoxyphenyl)-5-ethoxy-2,8-dimethyl-1,4-dihydro-1,6-naphthyridine-3-carboxamide (Ib) were added to 2.0 L (1564.06 g) of acetone and then 48.28 mL (6 equivalents, 47.75 g) of DBU were added thereto. The mixture was degassed in an ultrasound bath for 10 min. This reaction mixture was then transferred (under nitrogen) to a storage vessel and rinsed with 0.6 L of acetone (591.01 g). The reaction mixture was then equilibrated for 15 minutes under nitrogen, at a flow rate of 120 L/h. The reaction was started by switching on the UV lamp. The total irradiation time was 12 h.

The following table shows the result of the racemization over 12 hours:

| Time (h) | % e.e. |
|---|---|
| 0.00 | 100 |
| 1.00 | 84.10 |
| 2.00 | 70.74 |
| 3.00 | 60.13 |
| 4.00 | 54.16 |
| 5.50 | 45.37 |
| 6.50 | 41.66 |
| 7.50 | 40.70 |
| 9.00 | 27.62 |
| 10.00 | 17.49 |
| 11.00 | 11.77 |
| 12.00 | 7.07 |

Example 8

Preparation of rac (I) (4S,4R)-4-(4-cyano-2-methoxyphenyl)-5-ethoxy-2,8-dimethyl-1,4-dihydro-1,6-naphthyridine-3-carboxamide from pyridine derivative (II)

Equipment: Photo loop reactor, UV lamp TQ 150 (new lamp), M282 shell tube, circulating pump, thermostat (50° C.), 5 mm layer thickness. Lamp checked prior to test. Argon on minimum via gas regulator. UV/VIS reaction monitoring: 1 mm flow-through cuvette installed between pump outlet and inlet to the reactor. Ocean Optics FLAME spectrometer, deuterium/halogen light source.

3.75 g of pyridine derivative (II) were dissolved in 250 mL of acetone and degassed in an ultrasound bath for 15 minutes. The reaction mixture is a clear, yellow solution. Then placed in the reactor in the storage vessel, kept under argon. (Flow rate 500 ml/min.).

The reaction mixture was then heated to 50° C. and equilibrated under argon for 30 min. Then, 9 mL (9.18 g, 6 equivalents) of DBU was added under argon (DBU was stored under nitrogen). The reaction mixture is a clear, yellowish solution. The irradiation was then started. After 5 h 34 min, the lamp was switched off after a plateau was displayed in the UV. Then, 2 equivalents of DBU (3 mL) were added, continuing the reaction. The total irradiation time was 6 h.
Result:

Rac-(I) rac-(4S,4R)-4-(4-cyano-2-methoxyphenyl)-5-ethoxy-2,8-dimethyl-1,4-dihydro-1,6-naphthyridine-3-carboxamide: Purity: 91.4% (HPLC)

Pyridine derivative (II): 1.5%

Example 9

Reproducibility of the Irradiation Batches

In an analogous manner, as described in Example 4a, several batches of different amounts and different solvents (acetone and acetonitrile) were used. The concentration is ca. 1%, and in each case 6 equivalents of DBU were used.

The products obtained after water precipitation were dried and then recrystallized from spirits (or ethanol). The crystallization was carried out as follows: Illustrative example:

30 g of racemate (I), which was obtained after work-up (concentration of the reaction solution, water precipitation, isolation and drying), was added to 600 ml of spirits, the suspension then being heated to gentle reflux (Tinner=75° C.); a yellow solution formed from an internal temperature of ca. 57° C. The mixture was further stirred at this temperature for 30 minutes. Then, the mixture was clarified by filtration through a P4 frit covered with kieselguhr (soaked with 50 ml of spirits) and washed with 50 ml.

The spirits were distilled off at reduced pressure, the volume being reduced ca. 5-fold. Towards the end of the distillation, crystallization began, and a readily stirrable, pale yellow coloured suspension was obtained. The mixture was left to cool to 23° C. The mixture was further stirred overnight at an internal temperature of 23° C. The mixture was then cooled to an internal temperature of 2° C. and stirred at this temperature for a further 2 hours. The crystals were isolated over a 45 mm P3 frit and washed once cold with 45 ml of spirits.

This was dried in a vacuum drying cabinet at 50° C. under nitrogen-supplied air at ca. 100 mbar. The results are summarized in the table below.

| Solvent | Batch amount (g) | Purity after water precipitation % (HPLC) | Enantiomeric excess prior to recrystallization % e.e. | Purity after recrystallization from spirits % (HPLC) | Yield % of theory after crystallization from spirits | Enantiomeric excess prior to recrystallization % e.e. |
|---|---|---|---|---|---|---|
| ACN | 60 | 97.45 | 1.26 | 98.54 | 61.3 | 0.0 |
| acetone | 30 | 98.2 | 0.06 | 99.05 | 70.0 | 0.0 |
| acetone | 30 | 98.0 | 0.04 | 98.78 | 67.1 | 0.0 |
| acetone | 37.5 | 96.2 | 0.02 | 97.75 | 66.1 | 0.0 |
| acetone | 40 | 96.9 | 0.06 | 99.02 | 61.2 | 0.0 |

Example 10

Preparation of finerenone (Ia) from recycled rac-product (I) from Example 4a (4S)-4-(4-cyano-2-methoxyphenyl)-5-ethoxy-2,8-dimethyl-1,4-dihydro-1,6-naphthyridine-3-carboxamide Example 10a (+)O,O-Dibenzoyl tartrate salt (IVa) Preparation of (4S)-4-(4-cyano-2-methoxyphenyl)-5-ethoxy-2,8-dimethyl-1,4-dihydro-1,6-naphthyridine-3-carboxamide (Ia)

14.3 g of the title compound from Example 4a (I) were initially charged in 127.1 g of spirits and 53.7 g of water were added. Subsequently, 7.4 g of (+)-O,O-dibenzoyl-D-tartaric acid were added. The somewhat yellowish coloured suspension was heated to an internal temperature of 75° C. over one hour (bath temperature is at 82-85° C.) and then stirred at this temperature for 3 hours. The oil bath was switched off and the internal temperature cooled to 22° C. in about 5 hours and the mixture was stirred further at this temperature overnight (if the stirrer was switched off, the crystals sedimented rather quickly). The suspension was isolated over a P4 frit (50 ml) and washed once with a mixture of 15.5 g of spirits and 6.5 g of water: Wet yield: 23.2 g. Drying was carried out overnight in a vacuum drying cabinet under nitrogen at 50° C. and <100 mbar, Yield: 14.0 g of tartrate salt (IVa) of (4S)-4-(4-cyano-2-methoxyphenyl)-5-ethoxy-2,8-dimethyl-1,4-dihydro-1,6-naphthyridine-3-carboxamide (Ia)

Analysis:
Purity >98% (HPLC)
Enantiomeric excess: 96.42% e.e.

Example 10b (4S)-4-(4-cyano-2-methoxyphenyl)-5-ethoxy-2,8-dimethyl-1,4-dihydro-1,6-naphthyridine-3-carboxamide, crude (Ia)

13.00 g of the title compound from Example 10a were suspended in 104.0 g of water and then 20.5 g of ethanol, tol. denat. (spirits) were added, the pH was pH=4.0. Heating was effected to an internal temperature of 50° C. over 1 hour and a bath temperature of 60-62° C. Over ~30 minutes, the suspension was adjusted to pH=7.3 with a sodium phosphate solution (100 g $Na_3PO_4$/1 L water). The suspension was then stirred at 50° C. internal temperature for 60 minutes and readjusted to pH=7.5 with a sodium phosphate solution (100 g $Na_3PO_4$/1 L water). The mixture was then stirred at internal temperature 50° C. for 180 minutes. The oil bath was switched off and left to cool. The mixture was further stirred overnight at 23° C. internal temperature. The crystals were isolated over a 50 mm P3 frit and washed once with a mixture of 4.0 g of ethanol and 20.4 g of water and then twice with 21 g of water each time.

Wet yield: 7.6 g. This was dried in a vacuum drying cabinet at 50° C. overnight under nitrogen-supplied air.

Yield: 6.3 g of the title compound.
Analysis:
Purity >99.21% (HPLC)
Enantiomeric excess: 97.21% e.e.

Example 10c (4S)-4-(4-cyano-2-methoxyphenyl)-5-ethoxy-2,8-dimethyl-1,4-dihydro-1,6-naphthyridine-3-carboxamide, pure (Ia)

5.0 g of the title compound from Example 10b was added to 100 ml (20-fold) of ethanol, toluene denatured (=spirits). The suspension was heated to gentle reflux, the internal temperature was at 75° C. and the bath temperature at~90-92° C. From ca. 70° C. internal temperature, the solution was fully dissolved. Stirring was continued at this temperature for one hour. The solvent was then distilled off under slightly reduced pressure (40° C. bath temperature) and concentrated up to ca. 5-fold (~25 ml). This was stirred overnight at room temperature, then cooled to an internal temperature of 1-2° C. and further stirred at this temperature for ca. 2 hours. The crystals were isolated over a 30 mm P4 frit, then washed twice each with 5 ml of cold ethanol, toluene denatured.

Wet yield: 5.2 g

Drying was effected overnight in a vacuum drying cabinet at 80° C. under nitrogen-air supply <100 mbar.

Yield: 4.4 g of the title compound

Analysis:
Purity >99.62% (HPLC)
Enantiomeric excess: 99.45% e.e.

The invention claimed is:
1. A method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

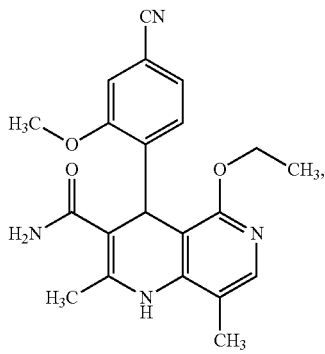
(I)

from the enantiomers of the formulae (Ia) and/or (Ib)

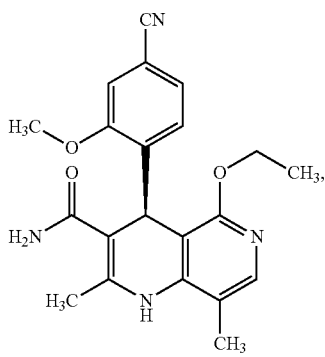
(Ia)

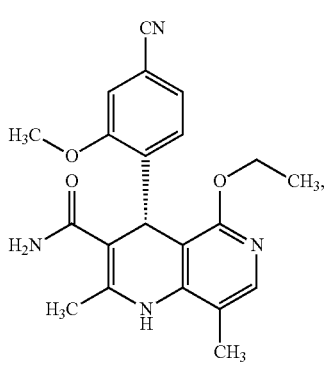
(Ib)

comprising the step of (i):
(i) irradiating the enantiomers of the formulae (Ia) and/or (Ib) with light in a suitable solvent or solvent mixture in the presence of a base,
wherein the irradiation in step (i) is effected optionally at a temperature of 0° C. to 100° C.
2. The method according to claim 1, wherein the irradiation with light in step (i) is effected at a temperature of 30° C. to 70° C.
3. The method according to claim 1, wherein the solvent or solvent mixture in step (i) is selected from the group consisting of dichloromethane, acetone, toluene, tetrahydrofuran, methanol, 4-methyl-2-pentanone, methyl ethyl ketone, cyclohexanone, acetonitrile, dimethylformamide, dimethylsulfoxide and mixtures thereof.
4. The method according to claim 1, wherein the concentration range of the enantiomer used in step (i) in the solvent or solvent mixture is 0.05% to 10% (m/v), based on the volume of the solvent or solvent mixture.
5. The method according to claim 1, wherein the base in step (i) is selected from the group consisting of 1,8-diazabicyclo[5.4.0]undec-7-ene (DBU), 1,5-diazabicyclo(4.3.0)non-5-ene (DBN), triethylamine, diisopropylethylamine, trimethylamine, tripropylamine, tributylamine, 1,4-diazabicyclo(2.2.2)octane (DABCO), 4-(dimethylamino)pyridine (DMAP), 1,5,7-triazabicyclo[4.4.0]dec-5-ene (TBD), 7-methyl-1,5,7-triazabicyclo[4.4.0]dec-5-ene (MTBD), tetramethylguanidine, N,N,N,N-tetramethyl-1,8-naphthalenediamine, lutidine, pyridine, imidazole, N-methylimidazole, phosphazene and mixtures thereof.
6. The method according to claim 1, wherein the irradiation in step (i) is effected for a period from 1 hour to 40 hours.
7. A method for preparing (4S)-4-(4-cyano-2-methoxyphenyl)-5-ethoxy-2,8-dimethyl-1,4-dihydro-1,6-naphthyridine-3-carboxamide of the formula (Ia)

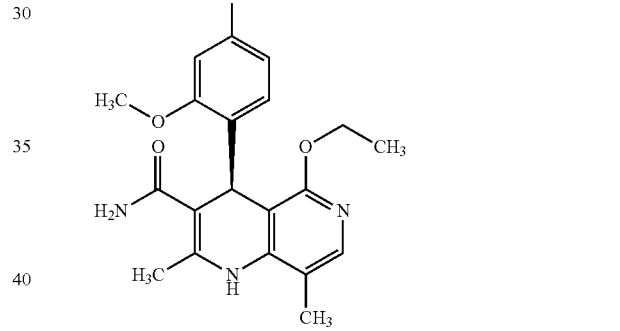
(Ia)

comprising the steps (ii), (iii) and (iv):
(ii) irradiating the compound of the formula (Ib)

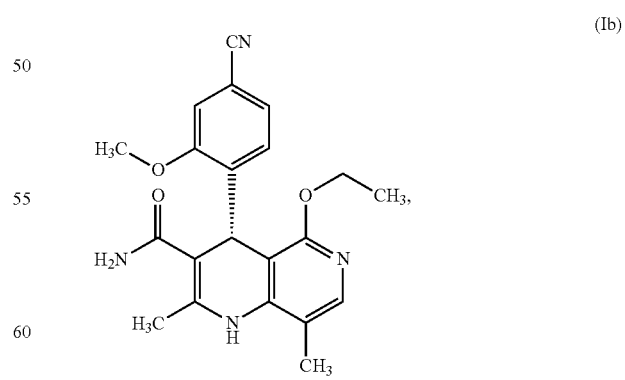
(Ib)

with light in a suitable solvent or solvent mixture in the presence of a base, wherein the compound of the formula (Ib) is converted to a racemic compound of the formula (I)

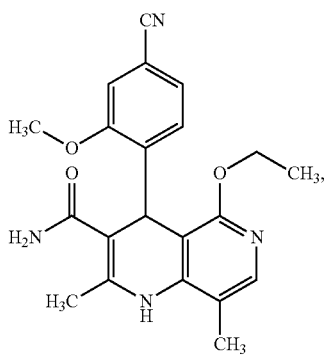

(iii) optical resolution of this racemic compound (I) from step (ii) using a chiral tartaric acid ester of the formula (III)

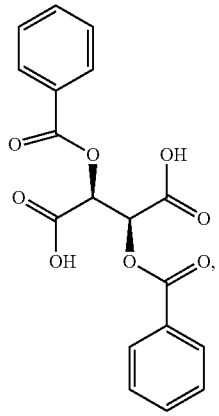

in a spirits/water mixture, wherein the diastereomeric salt (Iva)

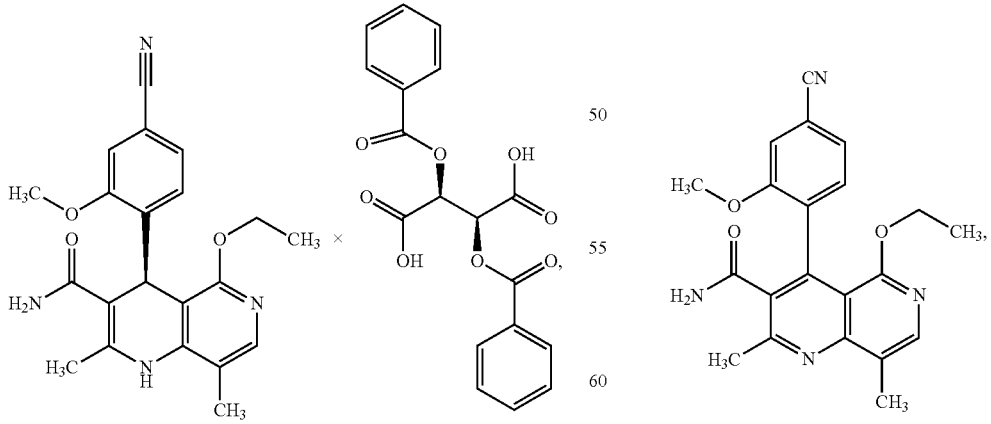

is formed, and (iv) treating the diastereomeric salt (Iva) from step (iii) with a base, wherein the compound of the formula (Ia) is formed.

8. The method according to claim 7, wherein the irradiation in step (ii) is effected at a temperature of 0° C. to 100° C.

9. The method according to claim 7, wherein the solvent or solvent mixture in step (ii) is selected from the group consisting of dichloromethane, acetone, toluene, tetrahydrofuran, methanol, 4-methyl-2-pentanone, methyl ethyl ketone, cyclohexanone, acetonitrile, dimethylformamide, dimethylsulfoxide and mixtures thereof.

10. The method according to claim 7, wherein the concentration range of the enantiomer used in step (ii) in the solvent or solvent mixture is 0.05% to 10% (m/v), based on the volume of the solvent or solvent mixture.

11. The method according to claim 7, wherein the base in step (i) is selected from the group consisting of 1,8-diazabicyclo[5.4.0]undec-7-ene (DBU), 1,5-diazabicyclo(4.3.0) non-5-ene (DBN), triethylamine, diisopropylethylamine, trimethylamine, tripropylamine, tributylamine, 1,4-diazabicyclo(2.2.2)octane (DABCO), 4-(dimethylamino)pyridine (DMAP), 1,5,7-triazabicyclo[4.4.0]dec-5-ene (TBD), 7-methyl-1,5,7-triazabicyclo[4.4.0]dec-5-ene (MTBD), tetramethylguanidine, N,N,N,N-tetramethyl-1,8-naphthalenediamine, lutidine, pyridine, imidazole, N-methylimidazole, phosphazene and mixtures thereof.

12. The method according to claim 7, wherein the irradiation in step (ii) is effected for a period from 1 hour to 40 hours.

13. A method for preparing racemic (4R,4S)-4-(4-cyano-2-methoxyphenyl)-5-ethoxy-2,8-dimethyl-1,4-dihydro-1,6-naphthyridine-3-carboxamide of the formula (I)

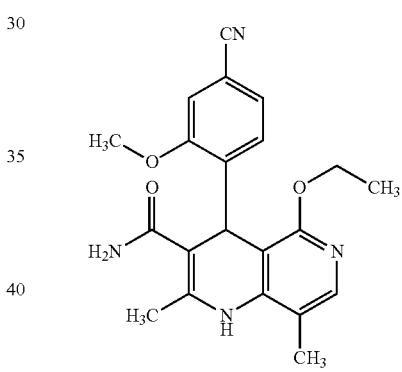

from the pyridine of the formula (II)

comprising the step (vi):
(vi) irradiating the compound of the formula (II) with light in a suitable solvent, or solvent mixture, in the presence of a base, wherein the compound according to formula (I) is formed.

14. The method according to claim 13, wherein the irradiation in step (vi) is effected at a temperature of 0° C. to 100° C. and/or wherein the irradiation in step (vi) is carried out for a period from 1 hour to 40 hours.

15. The method according to claim 13, wherein the solvent or solvent mixture in step (vi) is selected from the group consisting of dichloromethane, acetone, toluene, tetrahydrofuran, methanol, 4-methyl-2-pentanone, methyl ethyl ketone, cyclohexanone, acetonitrile, dimethylformamide, dimethylsulfoxide and mixtures thereof and/or wherein the base in step (iv) is selected from the group consisting of 1,8-diazabicyclo[5.4.0]undec-7-ene (DBU), 1,5-diazabicyclo(4.3.0)non-5-ene (DBN), triethylamine, diisopropylethylamine, trimethylamine, tripropylamine, tributylamine, 1,4-diazabicyclo(2.2.2)octane (DABCO), 4-(dimethylamino)pyridine (DMAP), 1,5,7-triazabicyclo[4.4.0]dec-5-ene (TBD), 7-methyl-1,5,7-triazabicyclo[4.4.0]dec-5-ene (MTBD), tetramethylguanidine, N,N,N,N-tetramethyl-1,8-naphthalenediamine, lutidine, pyridine, imidazole, N-methylimidazole, phosphazene and mixtures thereof.

* * * * *